United States Patent
Asai et al.

(10) Patent No.: US 12,272,443 B2
(45) Date of Patent: Apr. 8, 2025

(54) MEDICAL INFORMATION CONTROL SYSTEM, SIGNAL PROCESSING DEVICE, AND MEDICAL INFORMATION CONTROL METHOD

(71) Applicant: Sony Group Corporation, Tokyo (JP)

(72) Inventors: Atsushi Asai, Tokyo (JP); Yuki Sugie, Tokyo (JP); Masahito Yamane, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 402 days.

(21) Appl. No.: 17/911,428

(22) PCT Filed: Aug. 30, 2021

(86) PCT No.: PCT/JP2021/031765
§ 371 (c)(1),
(2) Date: Sep. 14, 2022

(87) PCT Pub. No.: WO2022/050227
PCT Pub. Date: Mar. 10, 2022

(65) Prior Publication Data
US 2023/0100302 A1    Mar. 30, 2023

(30) Foreign Application Priority Data
Sep. 1, 2020 (JP) .................. 2020-147074

(51) Int. Cl.
*G16H 30/40* (2018.01)
*G16H 30/20* (2018.01)

(52) U.S. Cl.
CPC ............ *G16H 30/40* (2018.01); *G16H 30/20* (2018.01)

(58) Field of Classification Search
CPC .............................. G16H 30/40; G16H 30/20
See application file for complete search history.

(56) References Cited

U.S. PATENT DOCUMENTS

| 11,322,248 | B2 * | 5/2022 | Grantcharov | G06F 17/40 |
| 2014/0303435 | A1 * | 10/2014 | Taniguchi | G06T 7/0016 |
| | | | | 600/103 |

(Continued)

FOREIGN PATENT DOCUMENTS

| JP | 2019-162231 A | 9/2019 |
| WO | 2019/116593 A1 | 6/2019 |

(Continued)

OTHER PUBLICATIONS

International Search Report and Written Opinion mailed on Oct. 26, 2021, received for PCT Application PCT/JP2021/031765, filed on Aug. 30, 2021, 6 pages.

*Primary Examiner* — Benjamin O Dulaney
(74) *Attorney, Agent, or Firm* — XSENSUS LLP

(57) ABSTRACT

Moreover, it is conceivable to support more advanced procedures by connecting a medical imaging device to a server and performing signal processing on the server.

According to an embodiment of the present disclosure, a medical information control system is provided in which an operation server includes a plurality of virtual shared buffers to which a first medical application installed in a first container virtual area and a second medical application installed in a second container virtual area are accessible, and a control application, and the control application controls the first medical application or the second medical application to alternately use a first virtual memory area, a second virtual memory area, and a third virtual memory area for write of the first medical application and read of the second medical application.

20 Claims, 16 Drawing Sheets

(56) References Cited

U.S. PATENT DOCUMENTS

| | | | |
|---|---|---|---|
| 2018/0228555 A1* | 8/2018 | Charron | A61B 90/361 |
| 2019/0385018 A1* | 12/2019 | Ngo Dinh | G06T 7/0012 |
| 2020/0236278 A1* | 7/2020 | Yeung | H04N 21/2187 |
| 2020/0297422 A1* | 9/2020 | Gocho | A61B 1/00055 |
| 2021/0052251 A1* | 2/2021 | Silberman | A61B 8/4245 |
| 2021/0154576 A1* | 5/2021 | Bhattacharyya | A63F 13/355 |
| 2021/0385558 A1* | 12/2021 | Walker | H04N 21/8547 |
| 2022/0354691 A1* | 11/2022 | Ben-Yishai | A61B 34/25 |
| 2023/0050833 A1* | 2/2023 | Cherubini | G06T 7/0012 |
| 2023/0351704 A1* | 11/2023 | McLachlan | G06V 20/20 |

FOREIGN PATENT DOCUMENTS

| | | |
|---|---|---|
| WO | 2019/181432 A1 | 9/2019 |
| WO | 2020/020959 A1 | 1/2020 |

* cited by examiner

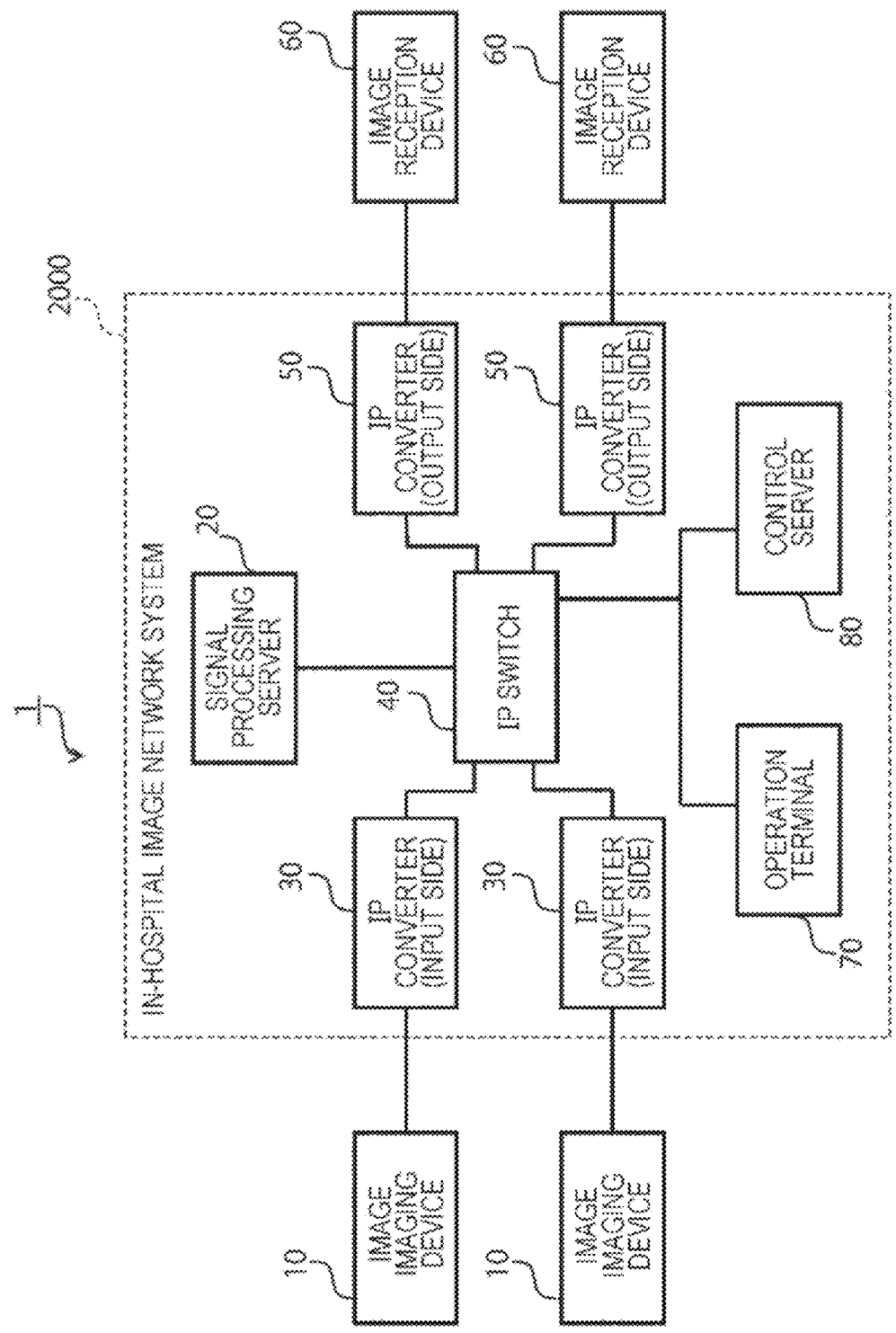
[Fig. 1]

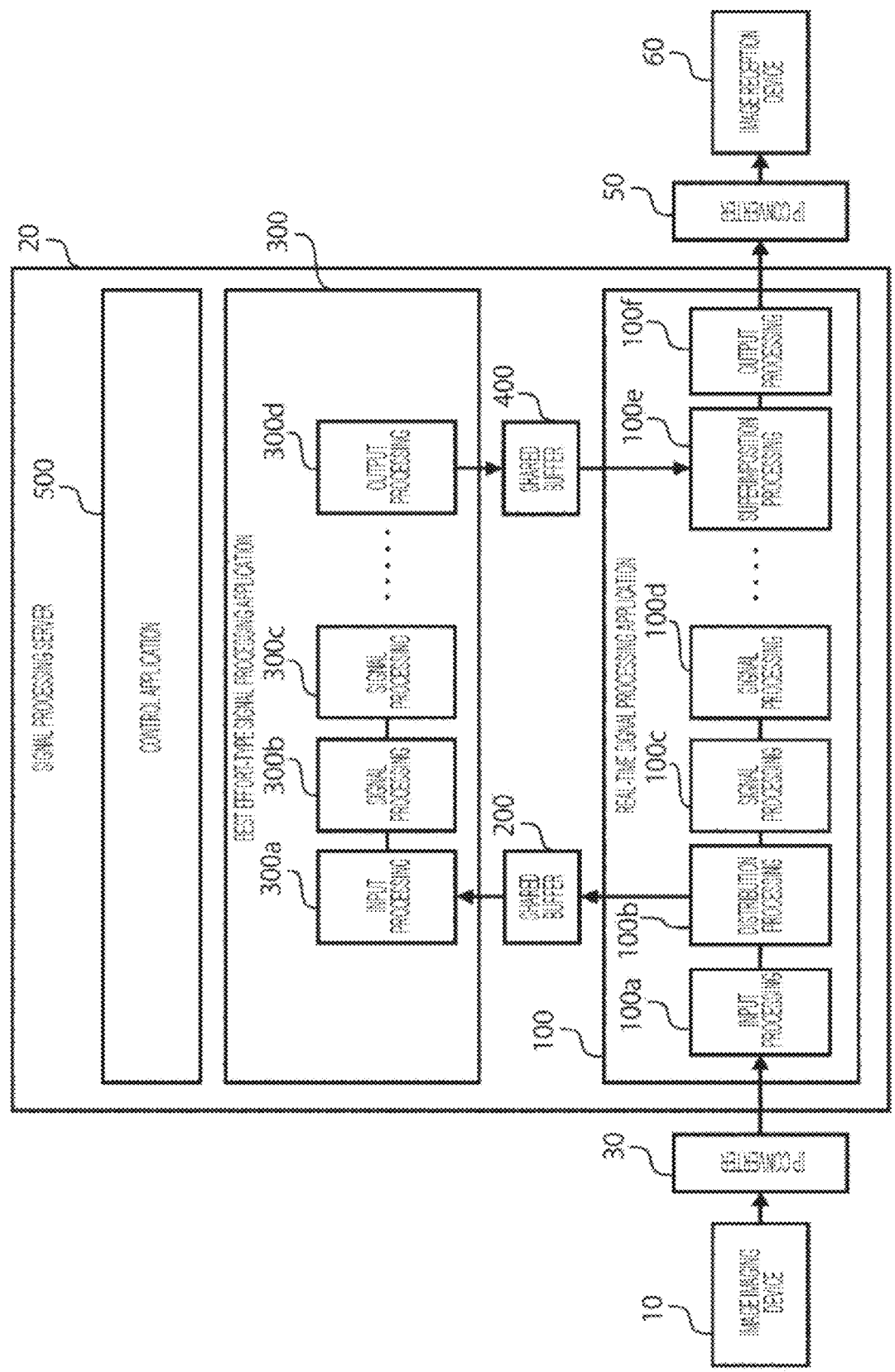

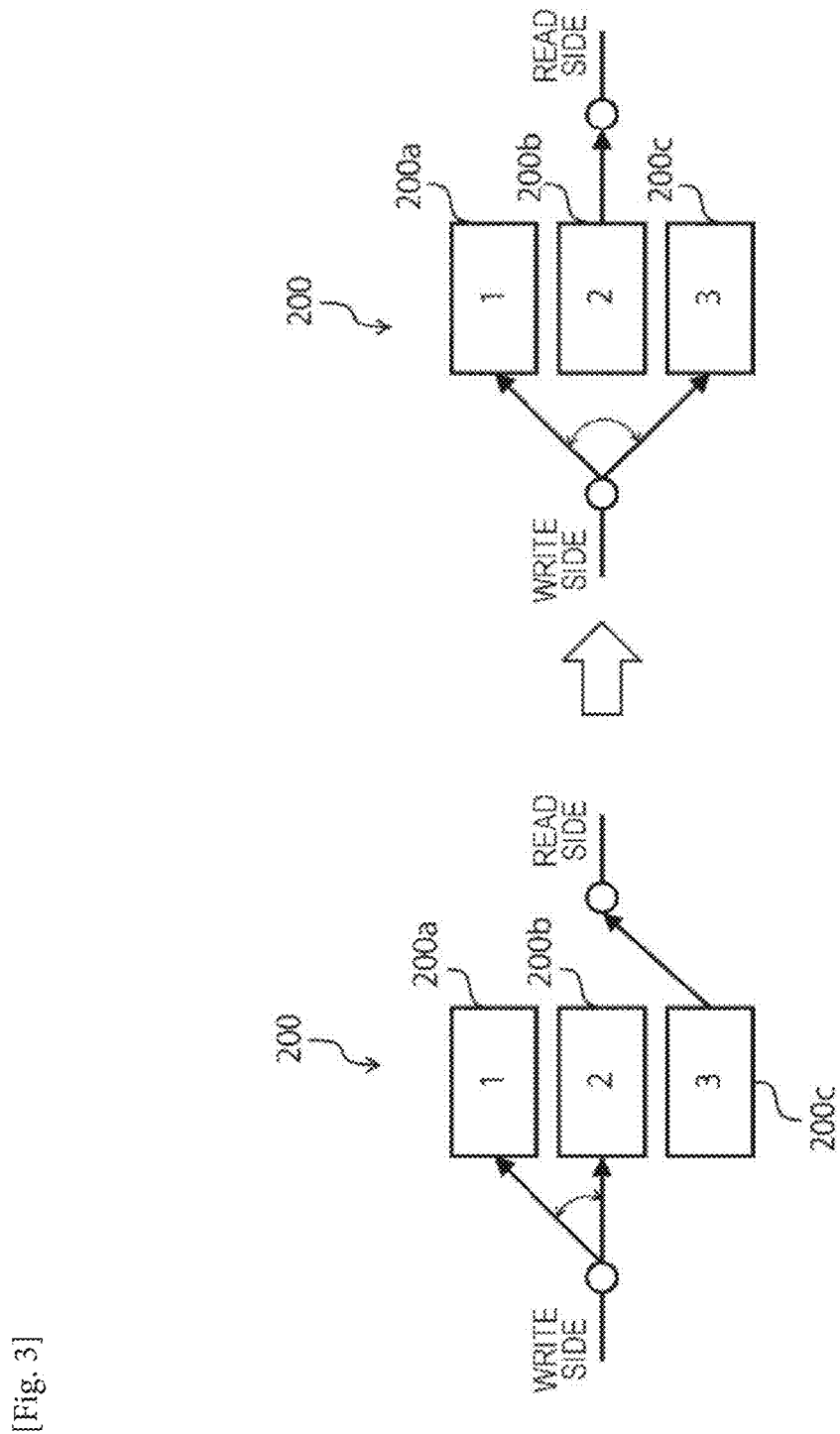
[Fig. 3]

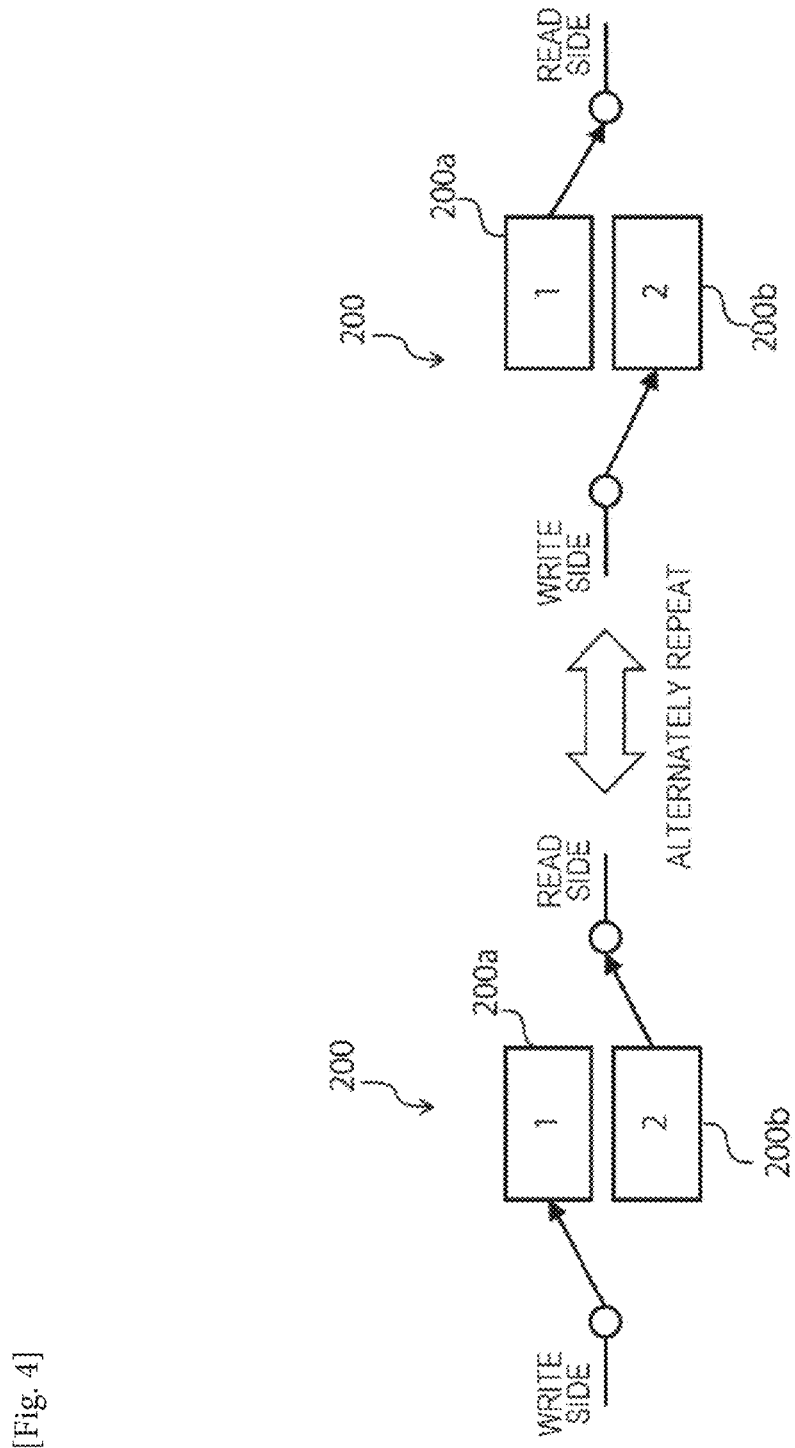
[Fig. 4]

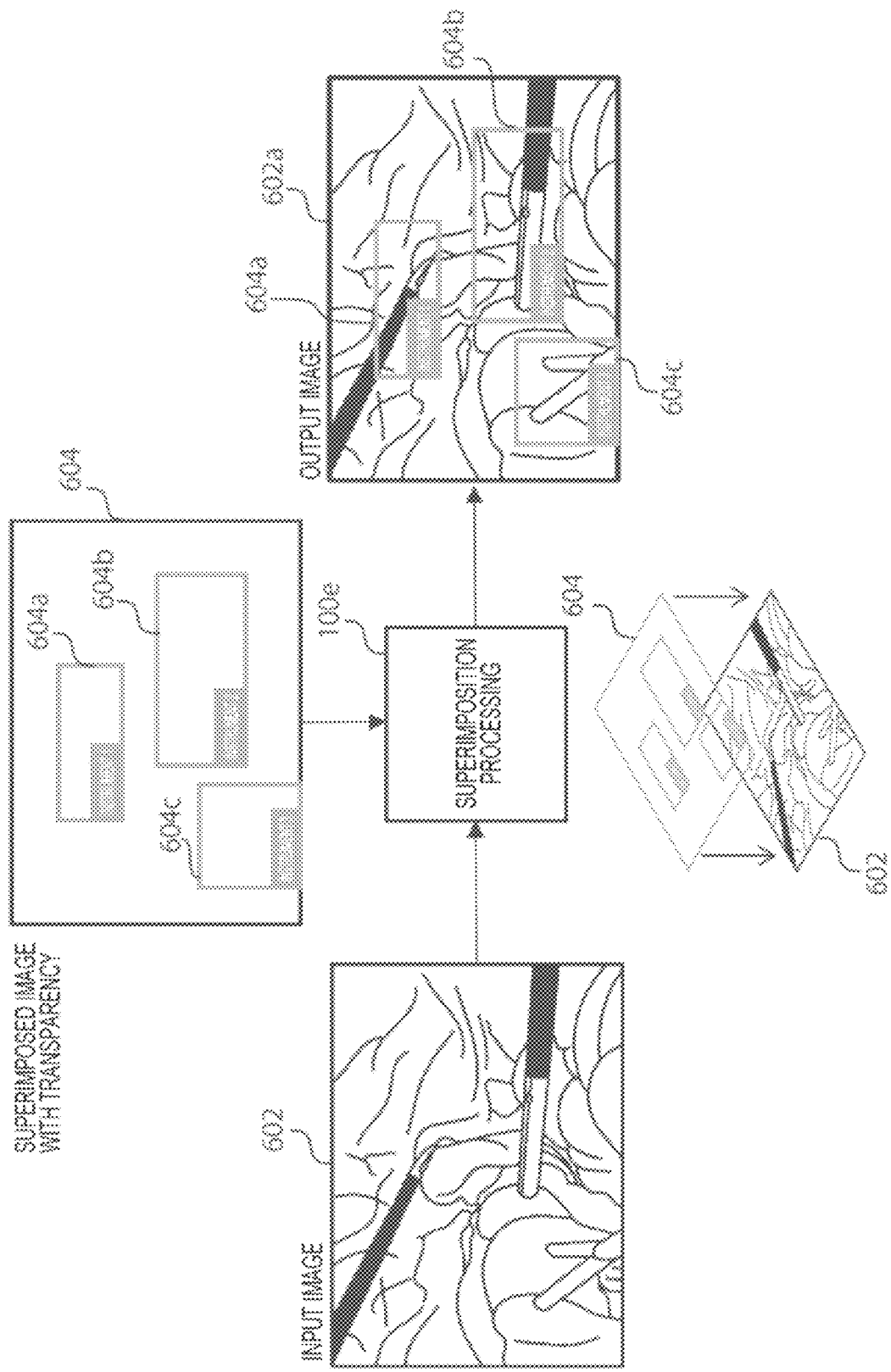

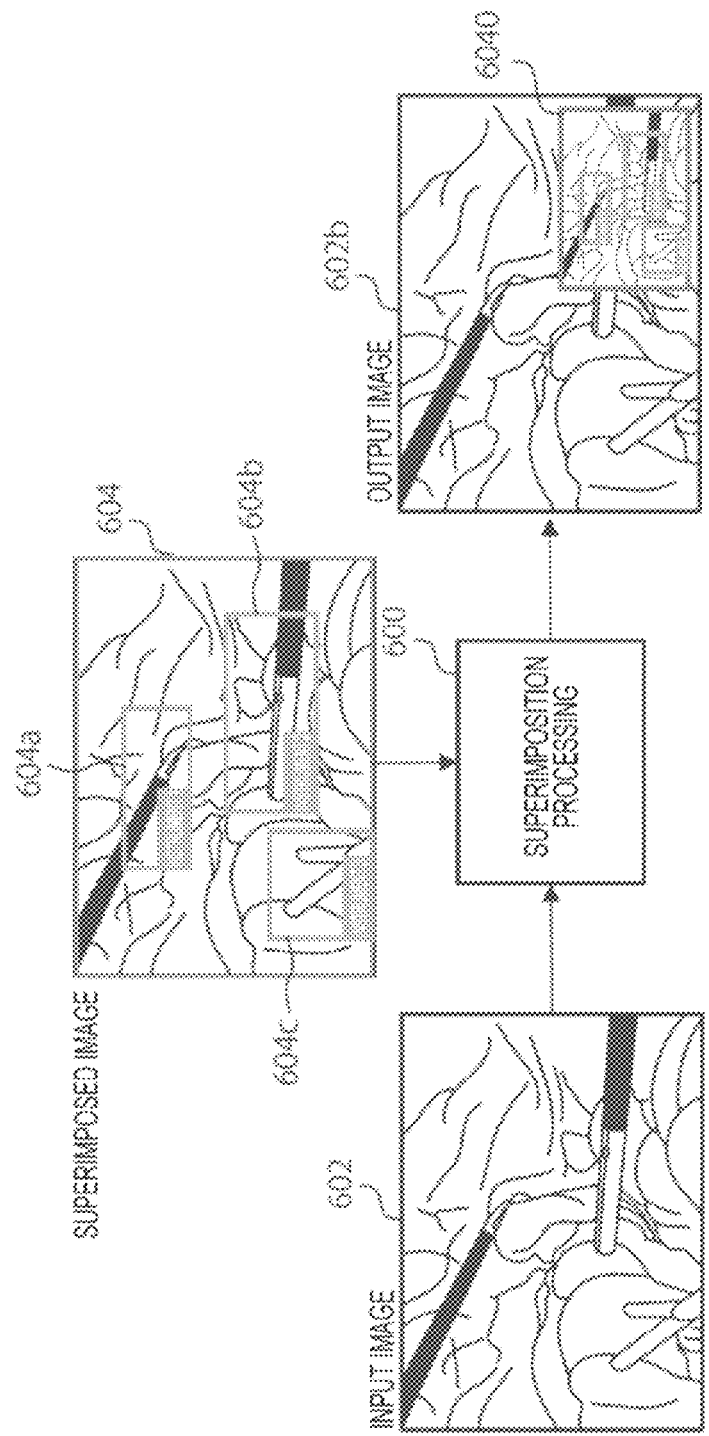

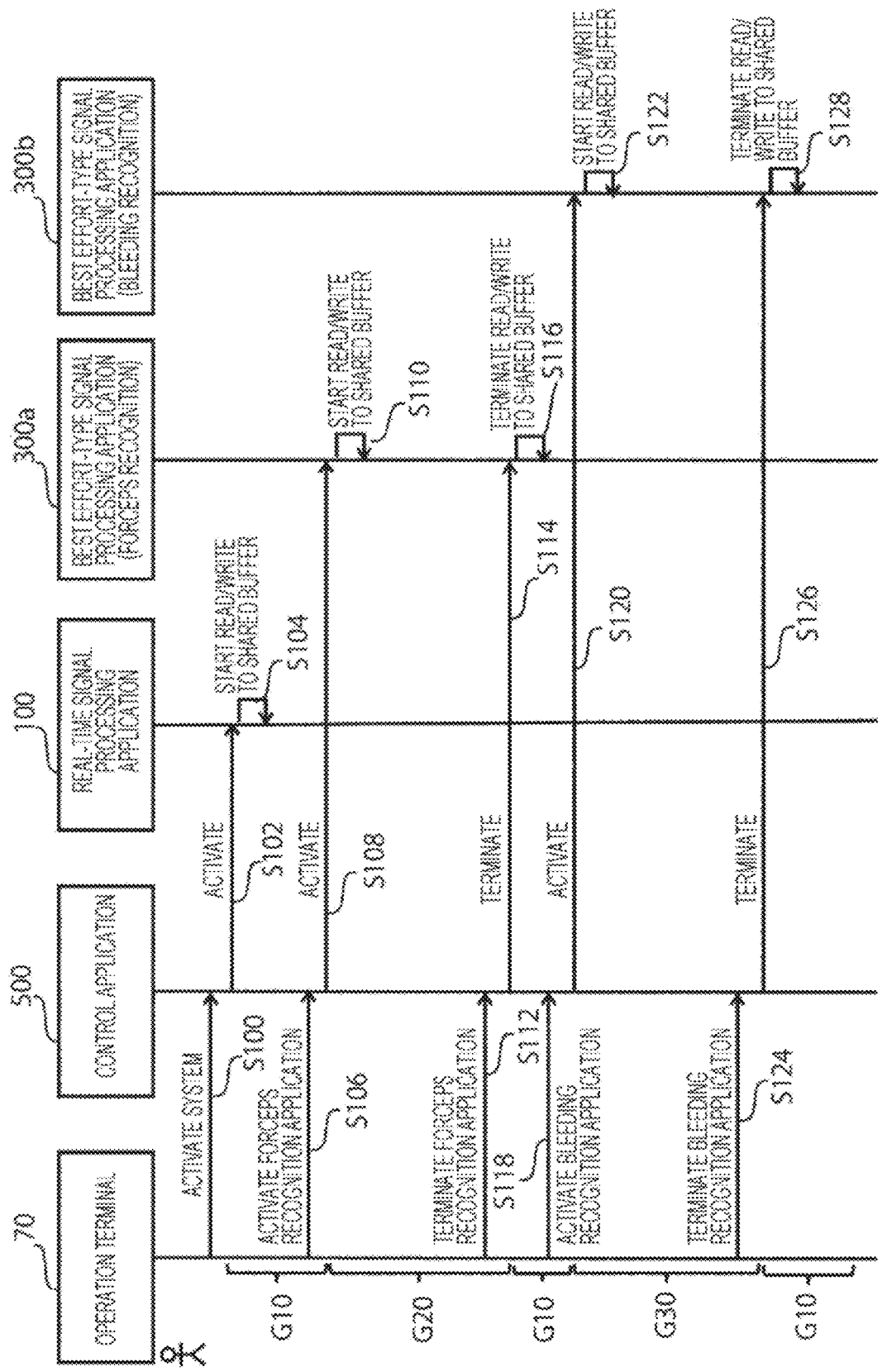

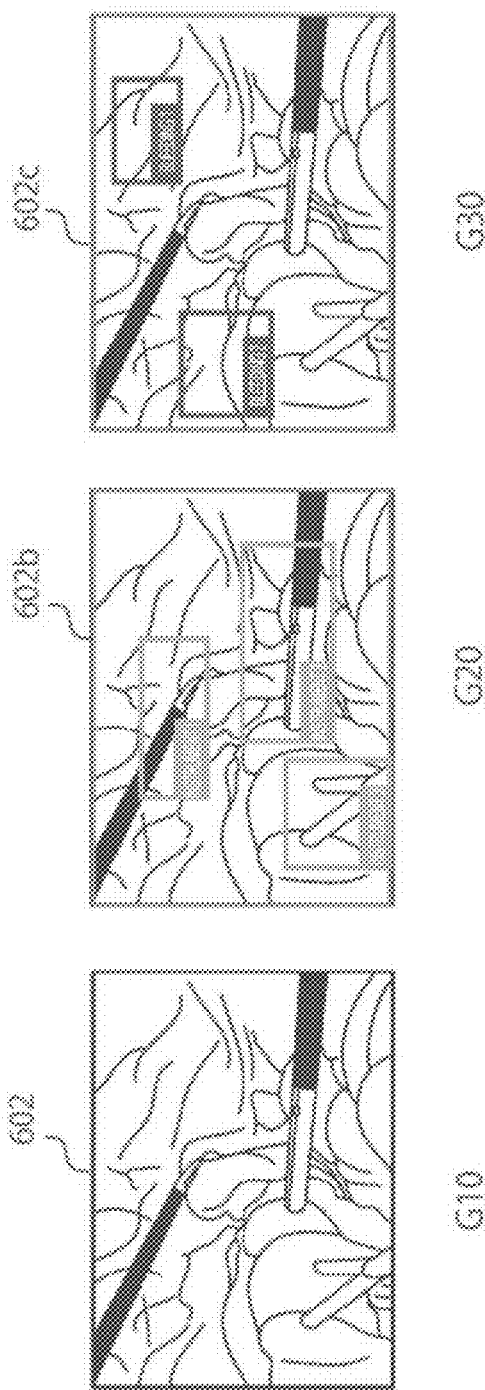
[Fig. 8]

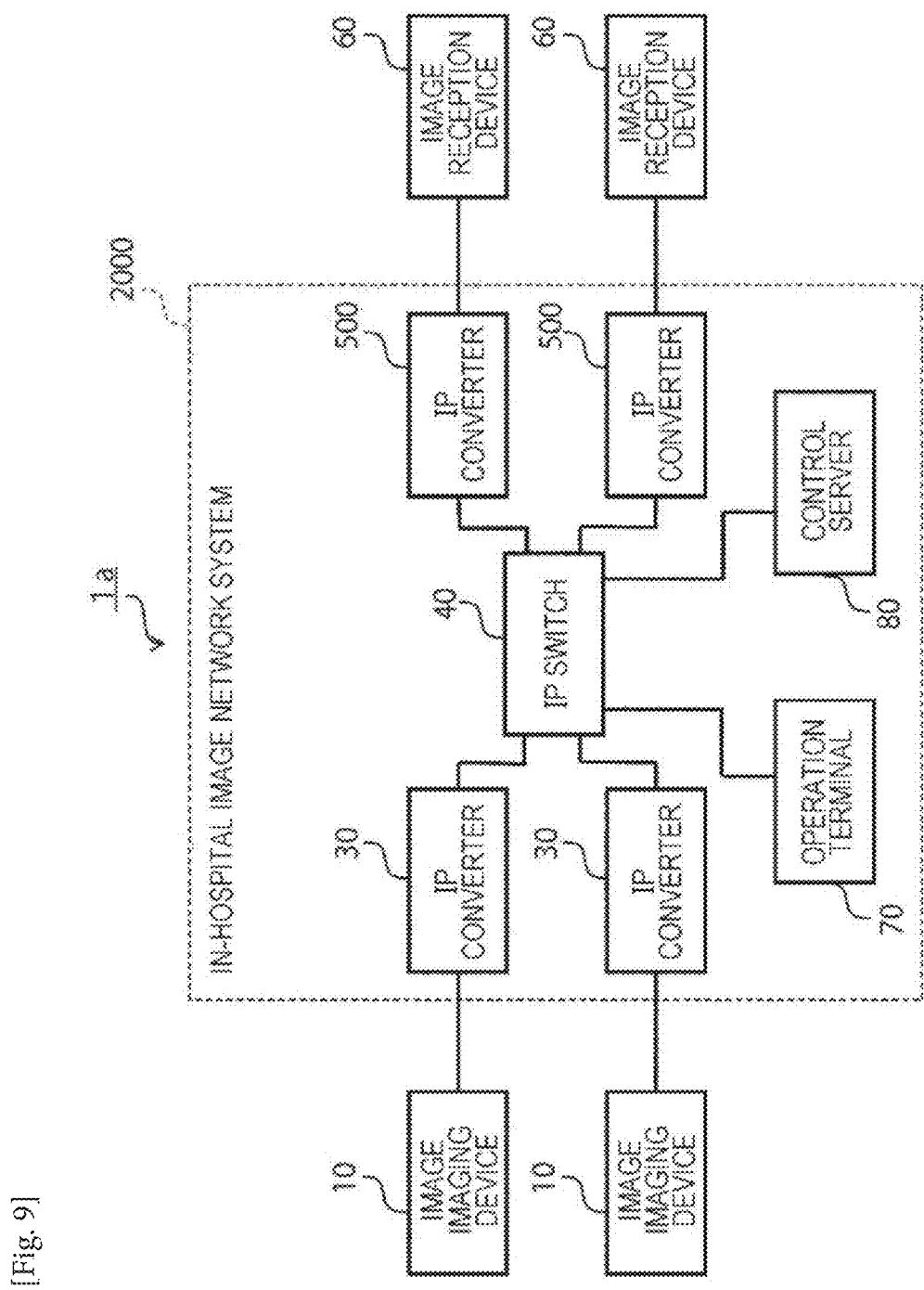
[Fig. 9]

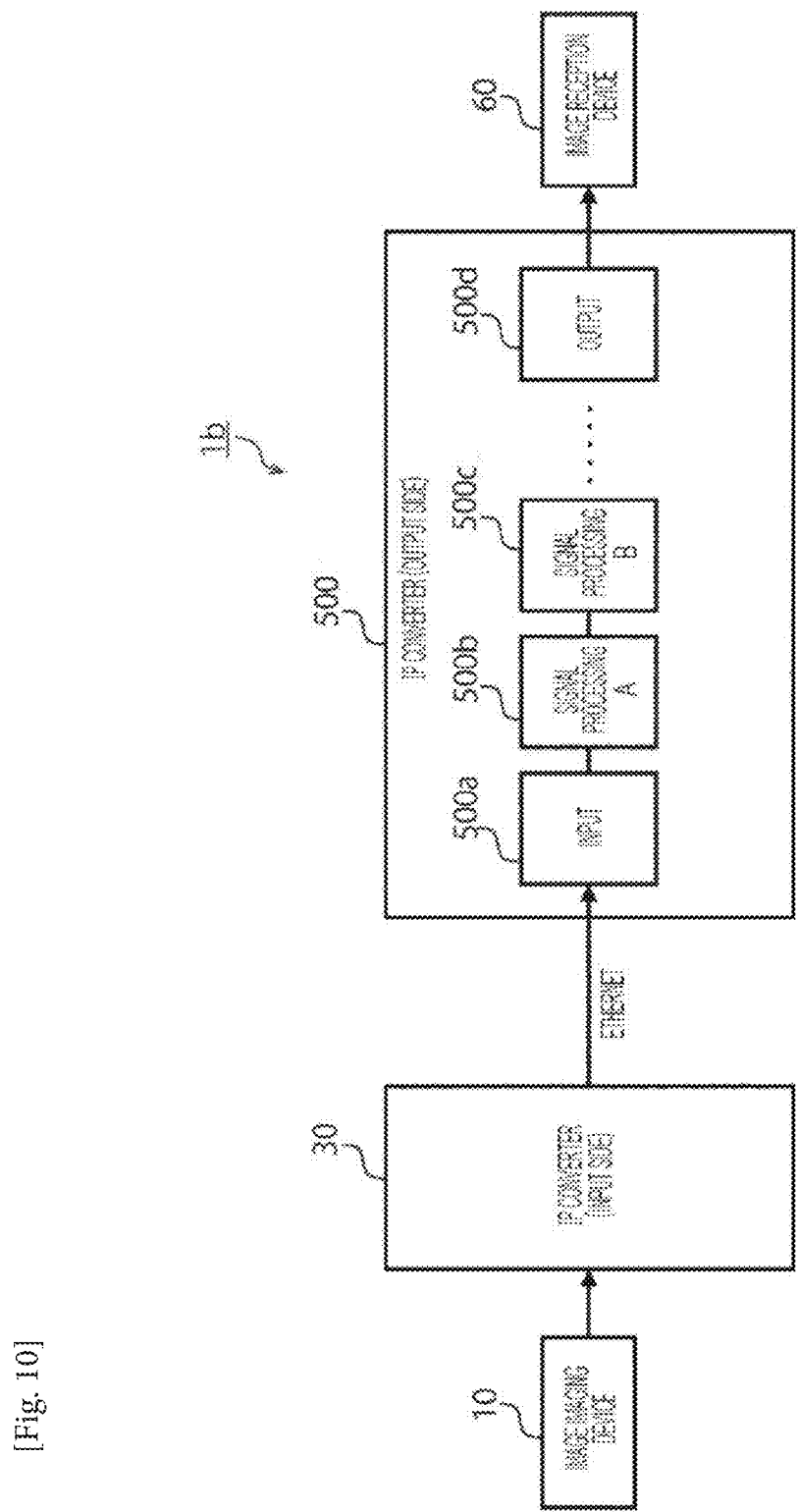
[Fig. 10]

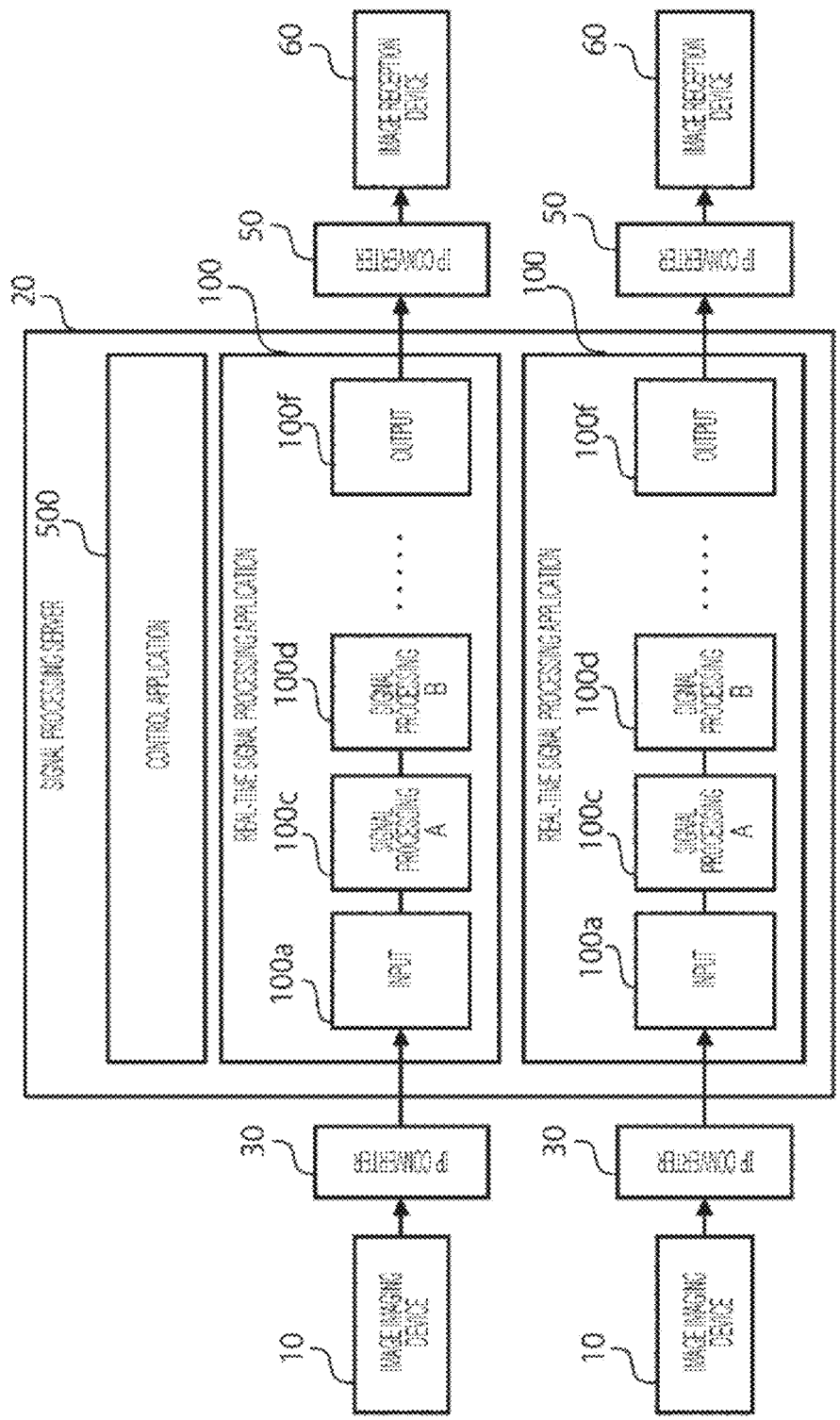

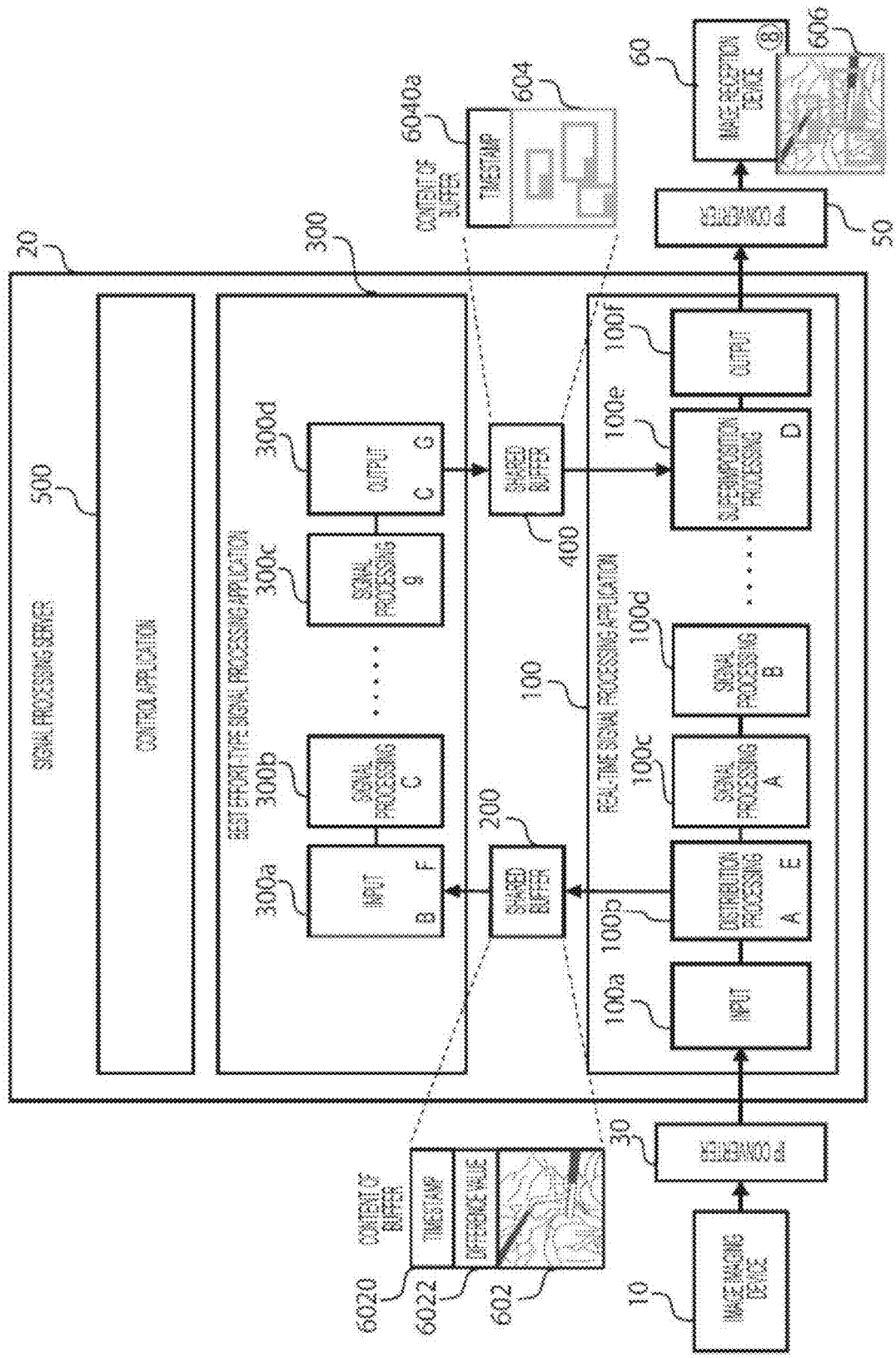
[Fig. 12]

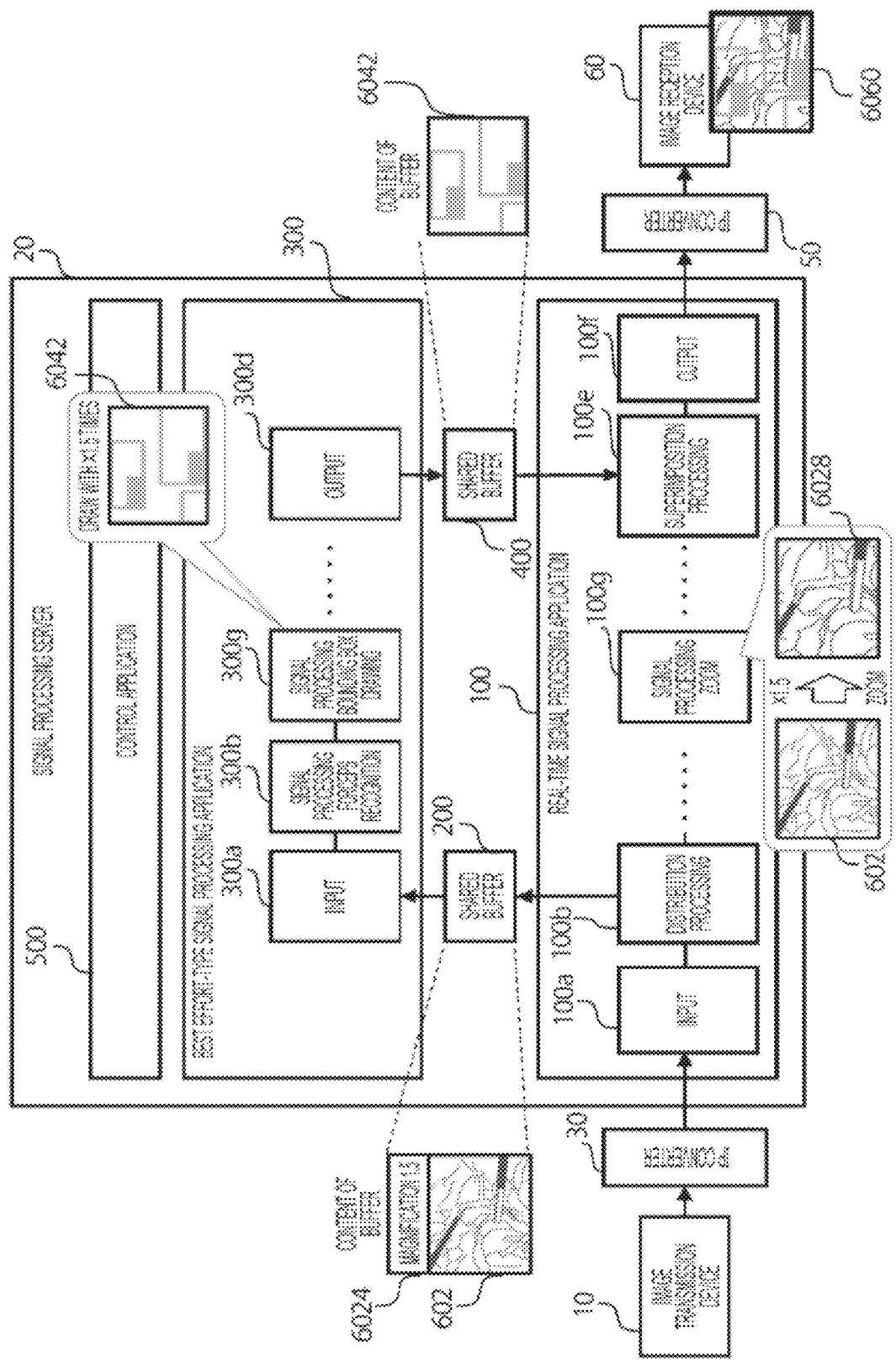
[Fig. 13]

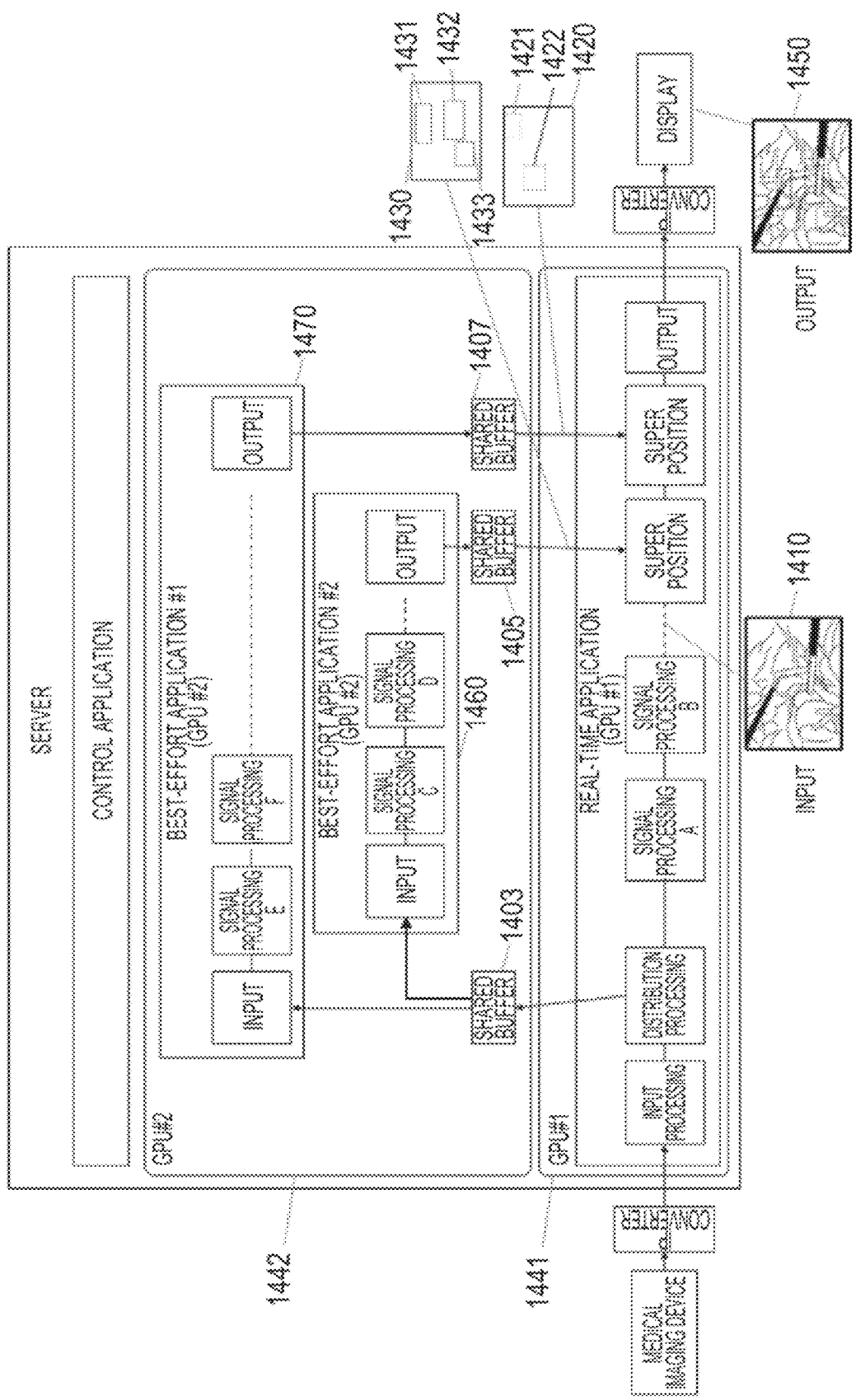

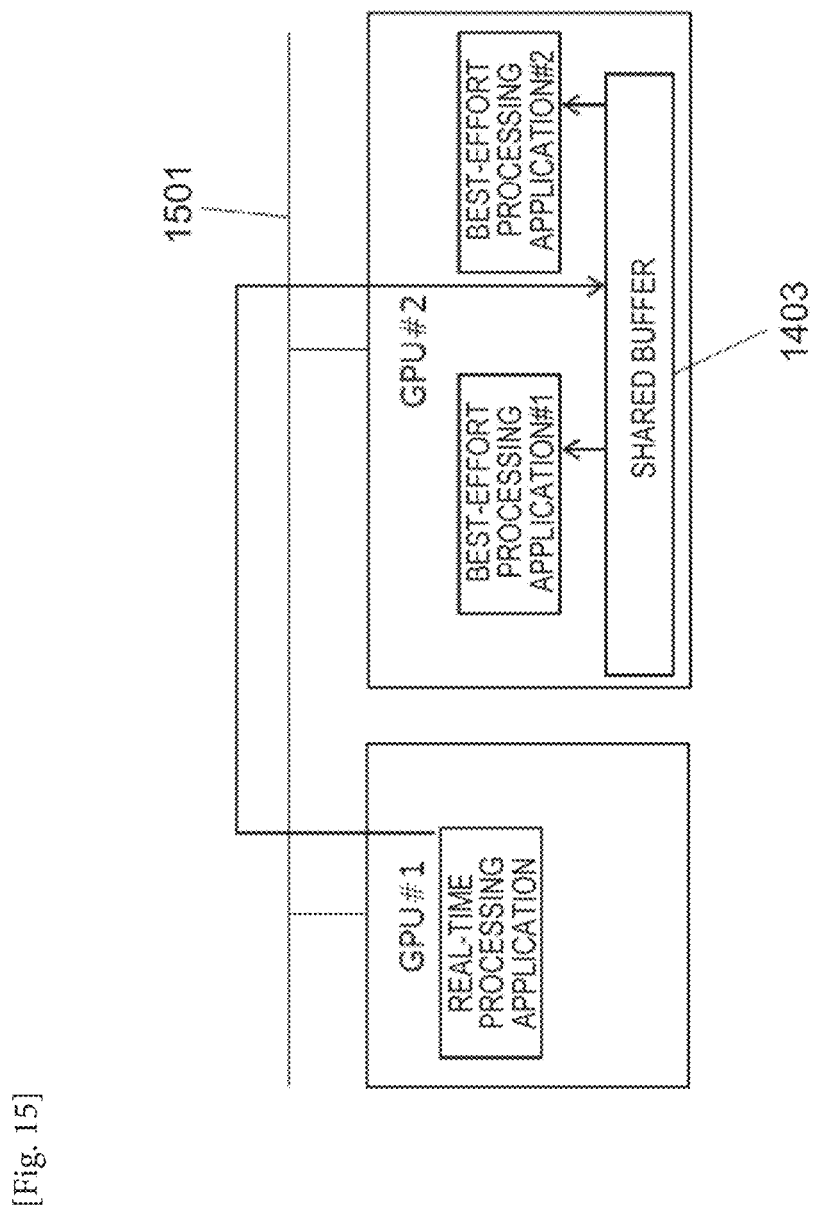
[Fig. 15]

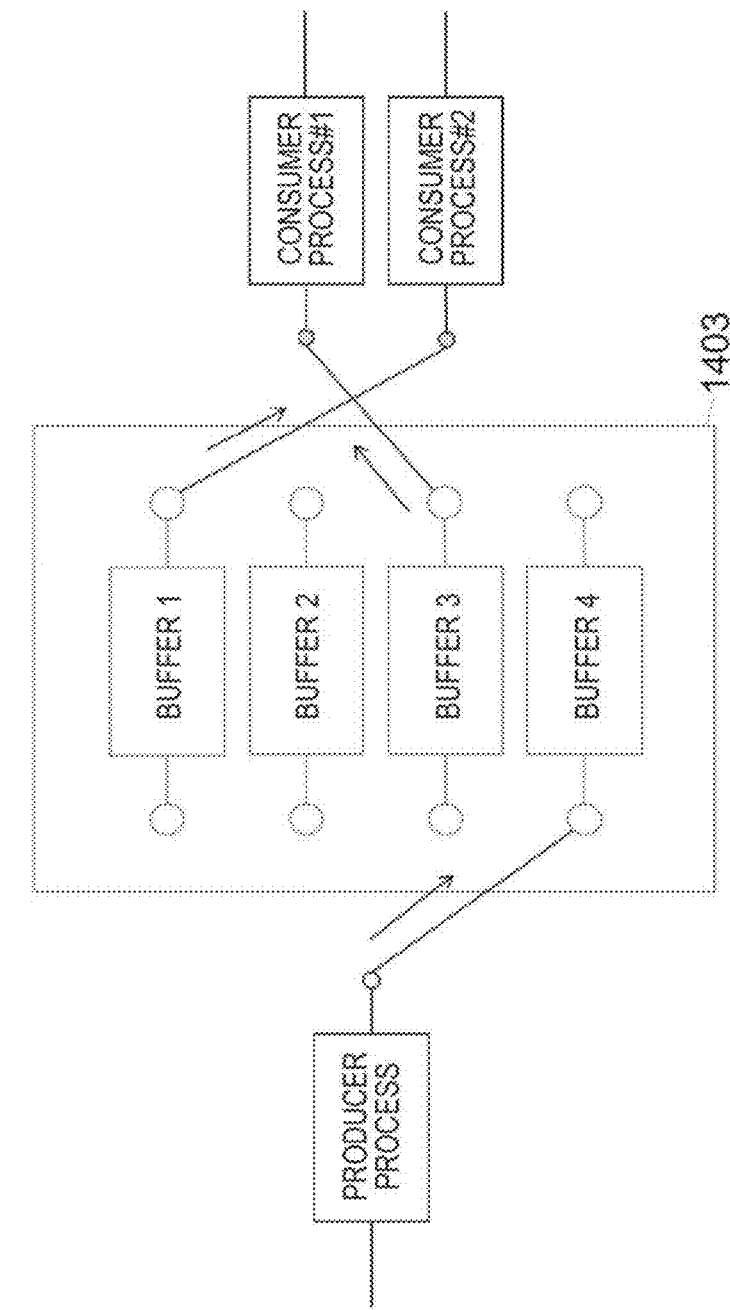
[Fig. 16]

MEDICAL INFORMATION CONTROL SYSTEM, SIGNAL PROCESSING DEVICE, AND MEDICAL INFORMATION CONTROL METHOD

CROSS-REFERENCE TO RELATED APPLICATIONS

The present application is based on PCT filing PCT/JP2021/031765, filed Aug. 30, 2021, which claims priority to Japanese Patent Application No. 2020-147074, filed Sep. 1, 2020, the entire contents of each are incorporated herein by reference.

TECHNICAL FIELD

The present disclosure relates to a medical information control system, a signal processing device, and a medical information control method.

BACKGROUND ART

Operations using a medical imaging device such as an endoscope or a video microscope are expected to enable more detailed procedures and to support the procedures by image processing technology. At this time, the image processing performed for medical images generated by the medical imaging device is desired to suppress hindrance of the procedures. Therefore, in the image processing, for example, real-time performance such as completion of the image processing for one frame within a certain time, and low latency such as short processing time required for image processing, that is, a small delay is required. Furthermore, displaying information useful for improving the efficiency of the procedures by complicated image processing is required at the same time.

Therefore, an external device (IP converter) that performs image processing such as rotation correction for medical images has been proposed (for example, PTL 1).

CITATION LIST

Patent Literature

PTL 1: JP 2019-162231A

SUMMARY

Technical Problem

Moreover, it is conceivable to support more advanced procedures by connecting a medical imaging device to a server and performing signal processing on the server.

Solution to Problem

According to an embodiment of the present disclosure, there is provided a medical information control system including:
an operation server connected to a medical imaging device in an operation room via a network, wherein the operation server includes processing circuitry configured to: obtain a medical imaging stream of a medical video generated by the medical imaging device,
execute, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable, and
superimpose the processing result of the best effort medical processing application on images contained in the medical imaging stream processed by the real-time medical processing application.

According to another embodiment of the present disclosure, there is provided a medical information control method including,
obtaining by an operation server connected to a medical imaging device in an operation room via a network a medical imaging stream of a medical video generated by the medical imaging device;
executing, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable; and
superimposing the processing result of the best effort medical processing application on images contained in the medical imaging stream processed by the real-time medical processing application.

BRIEF DESCRIPTION OF DRAWINGS

FIG. 1 is a diagram illustrating an example of a configuration of a medical information control system according to an embodiment of the present disclosure.

FIG. 2 is a block diagram illustrating a configuration example of a signal processing server.

FIG. 3 is a diagram illustrating a configuration and a processing example of a virtual shared buffer.

FIG. 4 is a diagram illustrating a configuration and a processing example using double buffering.

FIG. 5 is a diagram illustrating an example of superimposition processing illustrated in FIG. 2.

FIG. 6 is a diagram illustrating another example of the superimposition processing illustrated in FIG. 2.

FIG. 7 is a diagram illustrating a processing sequence example of the present embodiment.

FIG. 8 is a diagram illustrating an example of forceps recognition and bleeding spot recognition.

FIG. 9 is a diagram illustrating a configuration example of a medical information control system according to Comparative Example 2.

FIG. 10 is a diagram illustrating a configuration example of a medical information control system according to Comparative Example 3.

FIG. 11 is a block diagram illustrating a configuration example of a signal processing server according to a modification of the first embodiment.

FIG. 12 is a block diagram illustrating a configuration example of a signal processing server according to a second embodiment.

FIG. 13 is a block diagram illustrating a configuration example of a signal processing server according to a third embodiment.

FIG. 14 is a block diagram illustrating a configuration example of a signal processing server according to a fourth embodiment.

FIG. 15 is a block diagram of a plurality of graphics processing units that each run at least one application on data shared between graphics processing units.

FIG. 16 is a blocked diagram of a shared buffer with 2 more internal buffers than processes that access the internal buffers.

DESCRIPTION OF EMBODIMENTS

Hereinafter, embodiments of a medical information control system, a signal processing device, and a medical information control method will be described with reference to the drawings. Hereinafter, main components of the medical information control system will be mainly described, but the medical information control system may have components and functions not illustrated or described. The following description does not exclude components or functions not illustrated or described.

In operations, there are some cases where both of real-time signal processing and best effort-type signal processing (sometimes referred to as best effort medical processing application) are required at the same time. The real-time signal processing puts importance on latency, such as correcting the brightness of medical images acquired from an operative endoscope, and the best effort-type signal processing puts importance on results even if a large amount of calculation is required, such as tumor discrimination by image recognition.

At this time, the real-time signal processing and the best effort-type signal processing are required to be simultaneously processed in parallel. Therefore, it is required to operate in parallel a real-time application in which a medical imaging device is connected to a signal processing server and the signal processing server is required to perform low latency processing, and a best effort-type application in which low latency is not strongly required but complicated calculation processing is required, and to display information useful for improving the efficiency of procedures while maintaining the real-time performance.

However, when a processing result of the real-time application and a processing result of the best effort-type application are reflected in one display image in the signal processing server, buffer processing is required due to a difference in processing speed between the real-time application and the best effort-type application.

First Embodiment

FIG. 1 is a diagram illustrating an example of a configuration of a medical information control system 1 according to an embodiment of the present disclosure. As illustrated in FIG. 1, the medical information control system 1 according to the present embodiment includes a plurality of image imaging devices 10, a signal processing server 20, a plurality of input-side internet protocol (IP) converters 30, and an IP switch 40, a plurality of output-side IP converters 50, a plurality of image reception devices 60, an operation terminal 70, and a control server 80. Furthermore, the plurality of input-side IP converters 30, the IP switch 40, the plurality of output-side IP converters 50, the operation terminal 70, and the control server 80 constitute a video network 2000 as a hospital image network system, for example.

The image imaging device 10 functions as an image transmission device. For example, the image imaging device 10 is also called modality and is a device used for capturing a medical image. For example, in a case where the image imaging device 10 is an endoscope, the image imaging device 10 has an endoscope camera head and a camera control unit (CCU). The image imaging device 10 is not limited to an endoscope, and may be one of various medical devices such as an operative field camera or a microscope. That is, the image imaging device 10 is not limited to an endoscope, and may be any device having a function to capture a medical image, and its configuration is not particularly limited.

Note that, in the present embodiment, a set of signal values associated with coordinate information is referred to as an image. Furthermore, in the present embodiment, the image may be referred to as image data or an image signal. In particular, a set of signal values associated with coordinate information corresponding to position information of an image pickup unit in an imaging unit, for example, a two-dimensional sensor in the image imaging device 10 is referred to as a medical image. That is, in the medical information control system 1, the medical image is processed as medical image data or a medical image signal.

The signal processing server 20 is a signal processing device. The signal processing server 20 is a signal processing device (computer) that executes signal processing such as image processing. The signal processing server 20 is, for example, a server device arranged outside an operation room, and is connected to the plurality of IP converters 30 arranged in different operation rooms via the IP switch 40 and the video network 2000. For example, the signal processing server 20 executes processing on the basis of a control command output from the control server 80 in response to an operation instruction via the operation terminal 70. Note that details of the signal processing server 20 will be described below. Furthermore, the signal processing server 20 according to the present embodiment corresponds to an operation server.

The arrangement of the signal processing server 20 in the medical information control system 1 is not limited to the above-described arrangement outside the operation rooms. For example, the arrangement form of the signal processing server 20 may be an on-premises form such as being arranged in an operation room or in a facility provided with an operation room or may be a cloud form of being arranged outside an operation room or outside a facility provided with an operation room. That is, the signal processing server 20 in the medical information control system 1 may be installed at any position as long as conditions related to the operation of the medical information control system 1 are satisfied. Note that, in a case where the signal processing server 20 is provided outside an operation room, a large cooling facility or the like that is difficult to be installed in the operation room can be used. Therefore, the image processing server can be improved in performance.

The IP converter 30 is a converter that converts an image signal supplied from the image imaging device 10 into an IP-transmissible signal, for example, an Ethernet (registered trademark) signal. Input and output on the side of the image imaging device 10 and the image reception device 60 are generally interfaces such as serial digital interface (SDI), high-definition multimedia interface (HDMI (registered trademark), or Display Port. That is, the IP converter 30 converts the image signal supplied from the interface such as SDI, HDMI, or Display Port into the IP-transmissible signal. The control server 80 controls which image reception device 60 the image imaging device 10 is connected to in response to the user's operation instruction via the operation terminal 70.

The IP switch 40 (optical switcher or the like) has a function to transmit a received signal to a predetermined device on the basis of the control command output from the control server 80 in response to the operation instruction via the operation terminal 70, for example. Thereby, the image signal supplied from the image imaging device 10 is converted into, for example, an Ethernet signal by the corresponding IP converter 30, and is output to the signal processing server 20 and the IP converter 50 by the IP switch 40. For example, the IP converters 30 and 50 and the IP switch 40 are connected by Ethernet or the like.

The IP converter 50 converts the IP-transmissible signal supplied from the IP switch 40 into a signal corresponding to SDI, HDMI (registered trademark), Display Port, or the like that is the input interface on the side of the image reception device 60, and supplies the signal to the corresponding image reception device 60. More specifically, the IP converter 50 converts the supplied IP-transmissible signal into a display image signal. Then, the IP converter 50 supplies the generated display image signal to the corresponding image reception device 60.

The image reception device 60 is, for example, a monitor. The image reception device 60 displays the medical image on the basis of the display image signal supplied from the IP converter 50. The operation terminal 70 includes, for example, a mouse and a keyboard. The operation terminal 70 inputs the operation signal to the control server 80 in response to the user's operation. The control server 80 is a control device (computer). The control server 80 controls the entire medical information control system 1 according to the operation signal from the operation terminal 70.

In this way, the video network 2000 is constructed as an Ethernet-based video network. The Ethernet-based video network can suppress a physical space. At this time, the image imaging device 10 and the image reception device 60 can be connected via the video network 2000 in an operation room or in a hospital, instead of being directly connected. Thereby, various videos to be used in an operation by an endoscope, an ultrasonic diagnostic device, or a biological information monitor can be displayed or switched on an arbitrary monitor.

By the way, various image imaging devices 10 are used in the operation room, and a medical imaging device may not have a desired image processing function. Therefore, in the present embodiment, the signal processing server 20 performs image processing for the medical image output from the image imaging device 10 to implement functions independent of individual devices and vendors. Furthermore, operability of the image imaging devices 10 for the image processing can be unified.

As described above, the medical information control system 1 is required to execute the image processing for the image supplied from the image imaging device 10 with a smaller delay (latency) so as not to interfere with the procedures. For example, in the image processing performed for the medical image, it is required to display a high-resolution image such as 4K on the image reception device 60 at a frame rate such as 60 fps. As described above, in the present embodiment, the signal processing for one frame performed within a certain time is referred to as real-time signal processing so as not to hinder observation. Furthermore, these performance requirements are collectively referred to as real-time performance.

Meanwhile, medical applications that support procedures by image recognition and the like by AI are also being put into practical use, in addition to the image processing as the real-time signal processing. A processing time of the processing may vary depending on its content. Furthermore, there are some cases where the processing may be performed at a lower frame rate or the frame rate may vary due to a high processing load in general. Meanwhile, the signal processing such as recognition processing does not necessarily require the real-time performance. In the present embodiment, the image processing that provides additional information for the procedures by image recognition or the like is referred to as best effort-type signal processing that is performed on a best-effort basis.

In operations, there are some cases where both of the real-time signal processing and the best effort-type signal processing are required at the same time. The real-time signal processing puts importance on latency, such as correcting the brightness of medical images acquired from an operative endoscope, and the best effort-type signal processing puts importance on results even if a large amount of calculation is required, such as tumor discrimination by image recognition. At this time, the real-time signal processing and the best effort-type signal processing are required to be simultaneously processed in parallel.

Therefore, in the present embodiment, the image imaging device 10 is connected to the signal processing server 20. The signal processing server 20 operates in parallel a real-time application in which low latency processing is required, and a best effort-type application in which low latency is not strongly required but complicated calculation processing is required, and displays information useful for improving the efficiency of procedures while maintaining the real-time performance.

Here, details of the signal processing server 20 will be described with reference to FIG. 2. FIG. 2 is a block diagram illustrating a configuration example of the signal processing server 20. The signal processing server 20 is a server capable of executing a real-time signal processing application 100 and a best effort-type signal processing application 300 in parallel.

As illustrated in FIG. 2, the signal processing server 20 includes the real-time signal processing application 100, a virtual shared buffer 200, the best effort-type signal processing application 300, a virtual shared buffer 400, and a control application 500. The signal processing server 20 is a server capable of creating a so-called virtual container, and the real-time signal processing application 100, the best effort-type signal processing application 300, and the control application 500 are arranged on the signal processing server as independent containers. That is, these applications are executed on separate containers. By containerizing the real-time signal processing application 100, the best effort-type signal processing application 300, and the control application 500 in this manner, the computer resources of the real-time signal processing application 100 and the best effort-type signal processing application 300 can be logically separated. More specifically, "Docker" developed by Docker, Inc. is an example of a virtual environment that supports containers.

Furthermore, in general, in such a virtual container environment, upper limits of the number of cores of a CPU and a memory to be used by the applications, the number of available GPUs, and the like can be specified. By using the virtual container environment, the resources necessary for the real-time signal processing application 100 are preferentially allocated, and the computer resources of the real-time signal processing application 100 and the best effort-type signal processing application 300 can be physically separated.

The real-time signal processing application 100 is an application capable of processing signals for one frame within a certain period of time, and performs input processing 100a, distribution processing 100b, a plurality of pieces of signal processing 100c and 100d, superimposition processing 100e, and output processing 100f by, for example, pipeline processing. The input processing 100a inputs a signal supplied from the IP converter 30. The distribution processing 100b distributes the input signal supplied by the input processing 100a to the virtual shared buffer 200 and the signal processing 100c. The plurality of pieces of signal processing 100c and 100d performs image processing such as noise removal, various distortion corrections, improvement of resolution, improvement of gradation, color reproduction and color enhancement, and digital zoom. Note that, in the present embodiment, as the signal processing, the image processing such as noise removal, various distortion corrections, improvement of resolution, improvement of gradation, color reproduction and color enhancement, and digital zoom is performed but the signal processing is not limited to the above processing.

The superimposition processing 100e superimposes an image supplied from the virtual shared buffer 400 on an image for which the plurality of pieces of signal processing 100c and 100d has been performed. For example, the superimposition processing 100e superimposes an image by a so-called alpha blend that combines two images by a coefficient α. The output processing 100f supplies the superimposed image to the IP converter 50.

The virtual shared buffer 200 is a buffer shared by the real-time signal processing application 100 and the best effort-type signal processing application 300, and the real-time signal processing application 100 writes an input image in the buffer and the best effort-type signal processing application 300 reads the written image.

The best effort-type signal processing application 300 is an application that performs image processing for providing additional information for procedures by image recognition or the like, and performs input processing 300a, a plurality of pieces of signal processing 300b and 300c, and output processing 300d by, for example, pipeline processing. The input processing 300a reads an image from the virtual shared buffer 200 and supplies the image to the plurality of pieces of signal processing 300b and 300c.

The plurality of pieces of signal processing 300b and 300c is object recognition processing by, for example, simultaneous localization and mapping (SLAM) or machine learning. For example, the plurality of pieces of signal processing 300b and 300c is recognition processing corresponding to forceps recognition processing, bleeding area recognition processing, and the like, and applies the forceps recognition processing, the bleeding area recognition processing, and the like to an image, and superimposes area information on a transparent image, for example. The use of the term transparent, does not mean that it cannot be seen, but that it is at least partially transparent so it can be seen along with the image that lies underneath it. The output processing 300d performs processing of writing the image generated by the plurality of pieces of signal processing 300b and 300c to the virtual shared buffer 400. Furthermore, the plurality of pieces of signal processing 300b and 300c may perform the forceps recognition processing and the bleeding area recognition processing, or the plurality of pieces of signal processing 300b and 300c may perform one of the forceps recognition processing and the bleeding area recognition processing.

The virtual shared buffer 400 is a buffer shared by the real-time signal processing application 100 and the best effort-type signal processing application 300. That is, the best effort-type signal processing application 300 writes the processed image to the buffer and the real-time signal processing application 100 reads the written image from the buffer. Details of the virtual shared buffer 200 and the virtual shared buffer 400 will be described below.

The control application 500 controls the real-time signal processing application 100, the virtual shared buffer 200, the best effort-type signal processing application 300, and the virtual shared buffer 400. Note that a control example of the control application 500 will be described below.

Here, configurations and processing examples of the virtual shared buffer 200 and the virtual shared buffer 400 will be described with reference to FIG. 3. FIG. 3 is a diagram illustrating a configuration and a processing example of the virtual shared buffer 200. Since the virtual shared buffer 400 has a similar configuration to the virtual shared buffer 200, the description thereof will be omitted.

As described above, since the processing speed of the real-time signal processing application 100 and the processing speed of the best effort-type application 300 are different, buffer processing is required. Therefore, the virtual shared buffer 200 and the virtual shared buffer 400 according to the present embodiment perform the buffer processing by so-called triple buffering. As illustrated in FIG. 3, the virtual shared buffer 200 has three virtual memory areas 200a, 200b, and 200c. Here, it is assumed that a write side is faster than a read side.

The left figure of FIG. 3 is a state in which the write side is writing to the first virtual memory area 200a, and the read side is reading from the third virtual memory area 200c. If the read from the third virtual memory area 200c has not been completed yet when the write side has completed the write to the first virtual memory area 200a, the write side writes to the second virtual memory area 200b without waiting for completion of the read. Hereinafter, similarly, the write is alternately performed to the first virtual memory area 200a and the second virtual memory area 200b until completion of the read from the third virtual memory area 200c. When the read from the third virtual memory area 200c has been completed, the read side reads from the virtual memory area that is not being written between the first virtual memory area 200a or the second virtual memory area 200b. The case where the virtual memory area that is not being written is the second virtual memory area 200b is illustrated in the right figure of FIG. 6. While the read side is accessing the second virtual memory area 200b, the write side alternately writes to the first virtual memory areas 200a and 200c. In this way, the virtual shared buffer 200 allows the write side and the read side to asynchronously execute processing.

Note that if the read-side processing is faster than the write-side processing in FIG. 3, such a situation is illustrated in the left figure of FIG. 3, and there is a possibility that information written in the second virtual memory area 200b remains older than the third virtual memory area 200c at the timing when the read side has completed the access to the third virtual memory area 200c. In such a case, data can be transferred in a temporally correct order by the read side reading from the third virtual memory area 200c again. As can be seen from the above, the write side can asynchronously perform processing without being affected by the processing speed of the read side, and the read side can typically read the latest data for which write has been completed.

As described above, the processing speed of the best effort-type application 300 can be avoided from affecting the processing speed of the real-time signal processing application 100 by sharing asynchronous data using the virtual shared buffer 200 and the virtual shared buffer 400 that perform the triple buffering.

FIG. 4 is a diagram illustrating a configuration and a processing example using double buffering for the virtual shared buffer 200 and the virtual shared buffer 400 as Comparative Example 1. As illustrated in FIG. 4, in so-called double buffering, data is shared between the write side and the read side by using the two first virtual memory areas 200*a* and 200*b*. In the double buffering, the write side and the read side typically access different buffers. For example, in the left figure of FIG. 4, the write side is writing data to the first virtual memory area 200*a*. Meanwhile, the read side is reading data from the second virtual memory area 200*b*. When the write and the read have been completed, the buffers for read and write are switched to each other at the same timing as illustrated in the right figure of FIG. 4. If data being written is read or data being read is written, a correct output is difficult to be obtained, but this can be prevented by using the double buffering as described above. As a problem of the double buffering, the buffers are switched at the same timing, so in a case where the write side and the read side are different in processing speed, the faster side needs to wait for the next processing until the slower side finishes, which may affect the performance.

Meanwhile, it is expected that the real-time signal processing application 100 operates at a high frame rate of 60 fps, and the best effort-type signal processing application 300 operates at a slower frame rate. That is, both the applications need to be able to asynchronously read and write to the shared buffers. Therefore, in a case where the shared buffers are implemented as the double buffering, even if the real-time signal processing application 100 tries to write to the shared buffer in the distribution processing of FIG. 4, the read of the best effort-type signal processing application 300 has not been completed yet, and the processing of the real-time signal processing application 100 is blocked (becomes a waiting state). As can be seen from the above, the real-time performance is difficult to be guaranteed by the configuration using the double buffering for the virtual shared buffer 200 and the virtual shared buffer 400. In contrast, in the medical information control system 1 according to the present embodiment, the processing speed of the best effort-type application 300 can be avoided from affecting the processing speed of the real-time signal processing application 100 by sharing asynchronous data using the triple buffering as described above.

Here, details of the superimposition processing 100*e* illustrated in FIG. 2 will be described with reference to FIG. 5. FIG. 5 is a diagram illustrating an example of the superimposition processing 100*e* illustrated in FIG. 2. Here, an example in which the best effort-type signal processing application 300 performs forceps recognition for a medical image will be described.

The signal processing 300*b* and 300*c* of the best effort-type signal processing application 300 recognizes forceps in an input image 602, using machine learning such as DL. Then, the signal processing 300*b* and 300*c* draws the bounding boxes (rectangles indicating position and size) 604*a*, 604*b*, and 604*c* on a superposed image 604 with transparency.

At this time, it is conceivable that the best effort-type signal processing application 300 only recognizes the forceps, passes the position and size to the real-time signal processing application 100, and the real-time signal processing application 100 draws the bounding boxes. However, this method requires drawing as many as the number of recognized forceps, and a required processing load is difficult to be estimated. Therefore, in a case where there are many objects to be drawn, the real-time performance may be affected.

In contrast, in the present embodiment, as illustrated in FIG. 5, a buffer of the superposed image 604 with transparency is prepared on the best effort-type signal processing application 300 side, and necessary drawing is performed on the buffer. Then, the best effort-type signal processing application 300 passes the superposed image 604 with transparency to the real-time signal processing application 100 via the virtual shared buffer 400.

The real-time signal processing application 100 generates a superposed image 602*a* by superimposing by alpha blending the received superposed image 604 with transparency on the input image 602 flowing through its own pipeline on the basis of information of the transparency.

By doing so, the real-time signal processing application 100 is only required to typically perform the alpha blending on the full screen without depending on the content of the processing performed by the best effort-type signal processing application 300. Therefore, the processing load is constant and can be easily estimated. Thereby, the real-time performance can be guaranteed. In this way, the best effort-type signal processing application 300 passes the superposed image 604 with transparency to the real-time signal processing application 100, and the real-time signal processing application 100 performs only the superimposition processing for the superposed image 604, whereby an upper limit of the processing load of the real-time signal processing application can be kept constant.

FIG. 6 is a diagram illustrating another example of the superimposition processing 100*e* illustrated in FIG. 2. Here, an example in which the best effort-type signal processing application 300 performs forceps recognition for a medical image will be described. In this case, a processing result of the best effort-type signal processing application 300 may be superimposed on a partial area 6040 of the input image 602 by picture in picture, as illustrated in FIG. 6, instead of performing the alpha blending on the entire screen. However, the method of performing the alpha blending on the full screen may be more expressive.

Note that, in the present embodiment, superimposition of images has been described. However, it is conceivable to control execution parameters of the real-time signal processing application 100 by transferring metadata in addition to the image data. As an example, cooperation that the real-time signal processing application 100 performs digital zoom as the image processing, and a zoom magnification is controlled by the processing result of the best effort-type signal processing application 300 is conceivable.

Here, a processing sequence of the present embodiment will be described with reference to FIGS. 7 and 8. FIG. 7 is a diagram illustrating a processing sequence example of the present embodiment. FIG. 8 is a diagram illustrating an example of forceps recognition and bleeding spot recognition. In addition to the forceps recognition, the signal processing 300*b* and 300*c* of the best effort-type signal processing application 300 performs bleeding recognition for a medical image as another example of the best effort-type signal processing application 300. The input image 602 is, for example, a medical image. The best effort-type signal processing application 300 recognizes bleeding spots in the input image 602, using machine learning such as DL, and draws bounding boxes (position and size) 610a and 610b of the bleeding spots on an output image 602c. Note that, in the present embodiment, an image may be referred to as image data.

As illustrated in FIG. 7, the user first activates the real-time signal processing application via the operation terminal 70 (step S100). At this time, the operation terminal 70 may communicate with the control application 500 of the signal processing server 20 via the control server 80, but here, the operation terminal 70 directly communicates with the signal processing server 20.

Next, the control application 500 activates the real-time signal processing application 100 (step S102). The real-time signal processing application 100 performs the image processing for the input image 602 input from the specified image imaging device 10 and outputs the image to the image reception device 60. An image of the output image at this point is illustrated in G10 in FIG. 8. At the same time, the real-time signal processing application 100 starts read and write to the virtual shared buffer 200 (step S104). However, since there is no shared application, the result image is not particularly effective.

Next, the user activates a forceps recognition application as the best effort-type signal processing application 300 for the control application 500 via the operation terminal 70 (step S106). When the forceps recognition application is started via the control application 500, the application performs forceps recognition for the image obtained from the virtual shared buffer 200 (step S108) and writes the result to the output-side virtual shared buffer 400 (step S110). There is no change in the processing content of the real-time signal processing application 100, but an output image 602b illustrated in G20 of FIG. 8 is obtained. The flow of the signal processing at this time is equivalent to the above-described state in FIG. 5, and the forceps recognition application corresponds to the best effort-type signal processing application 300.

Next, the user is assumed to switch the forceps recognition application to a bleeding recognition application. The user performs an operation of terminating the forceps recognition application for the control application 500 via the operation terminal 70 (step S112). Then, the control application 500 terminates the forceps recognition application (step S114). At this time, the forceps recognition application clears the output-side virtual shared buffer 400 and then terminates the read and write so that the output image does not remain (step S116).

Next, the user activates the bleeding recognition application for the control application 500 via the operation terminal 70 (step S118). When the bleeding recognition application is started via the control application 500, the application performs bleeding recognition for the image obtained from the virtual shared buffer 200 (step S120) and writes the result to the output-side virtual shared buffer 400 (step S122). There is no change in the processing content of the real-time signal processing application 100, but an output image 602c illustrated in G30 of FIG. 8 is obtained. The flow of the signal processing at this time is equivalent to a flow in which the content of the best effort-type signal processing application is changed from the forceps recognition application to the bleeding recognition application in FIG. 5.

After that, when the user terminates the bleeding recognition application (step S124, step S126, and step S128), the output image returns to the state of G10 in FIG. 8.

Even if the best effort-type signal processing application 300 is activated, terminated, or switched in this way, the processing content and load of the real-time signal processing application 100 do not change. That is, since the same distribution processing and superimposition processing are only continued, image disturbance and frame rate variation due to switching do not occur, and the real-time performance of the real-time signal processing application 100 is guaranteed.

FIG. 9 is a diagram illustrating a configuration example of a medical information control system 1a according to Comparative Example 2. As illustrated in FIG. 9, the medical information control system 1a according to Comparative Example 2 includes a plurality of image imaging devices 10, a plurality of transmission-side IP converters 30, an IP switch 40, and a plurality of reception-side IP converters 500, and a plurality of image reception devices 60. Furthermore, the IP converter 500 executes the image processing.

As illustrated in FIG. 9, the medical information control system 1a according to Comparative Example 2 does not have a signal server that performs the signal processing. Therefore, in the medical information control system 1a according to Comparative Example 2, the CCU of the image imaging device 10 executes the functions of the real-time signal processing and the best effort-type signal processing. As a result, in the medical information control system 1a according to Comparative Example 2, the functions in the image imaging device 10 become bloated, leading to an increase in development and quality control costs. In addition, by providing similar functions for each device vendor, the operability is not unified and the usability deteriorates.

In contrast, in the medical information control system 1 according to the present embodiment, the medical image input from the image imaging device 10 to the signal processing server 20 is an image in a general format such as SDI or HDMI (registered trademark) as described above. Therefore, the functions independent of the individual devices and vendors can be implemented. As a result, the functions can be shared by all vendors, and the operability is unified. Furthermore, since the signal processing server 20 can uniformly perform the signal processing for the image imaging devices 10, the functions in the image imaging device 10 can be suppressed, and the development and quality control costs can be reduced.

FIG. 10 is a diagram illustrating a configuration example of a medical information control system 1b according to Comparative Example 3. As illustrated in FIG. 9, the medical information control system 1b according to Comparative Example 3 includes an image imaging device 10, a transmission-side IP converter 30, a reception-side IP converter 500, and an image reception device 60. Furthermore, the IP converter 500 executes the signal processing. That is, the IP converter 500 performs input processing 500a, a plurality of pieces of signal processing 500b and 500c, and output processing 500d. As described above, since the image input from the image imaging device 10 to the IP converter 500 is an image in the general format such as SDI or HDMI (registered trademark), the functions independent of individual devices and vendors can be implemented. As a result, the functions can be shared by all vendors, and the operability is unified.

Meanwhile, since the IP converter 500 is generally small and has limited computing power, implementable signal processing performance and functions such as the image processing are limited. In particular, in the case of image recognition using machine learning, such as detecting a specific object or situation from an image, the processing load is generally high. Furthermore, the processing load varies depending on the content of the image, and the real-time performance when displaying the medical image output from the image imaging device 10 is impaired. In contrast, the medical information control system 1 according to the present embodiment performs the signal processing by the signal processing server 20. In this case, as described above, the processing content and load of the real-time signal processing application 100 do not change by the triple buffering even if the best effort-type signal processing application 300 is activated, terminated, or switched. Therefore, the real-time signal processing application 100 according to the present embodiment simply continues the same distribution processing and superimposition processing, and thus the image disturbance and frame rate variation due to switching do not occur, and the real-time performance can be guaranteed.

As described above, according to the present embodiment, the signal processing server 20 includes the plurality of virtual shared buffers 200 and 400 to which the real-time signal processing application 100 installed in a first container virtual area and the best effort-type signal processing application 300 installed in a second container virtual area are accessible, and the control application 500. Then, each of the virtual shared buffers 200 and 400 has the first virtual memory area 200a, the second virtual memory area 200b, and the third virtual memory area 200c, and the control application 500 controls the real-time signal processing application 100 and the best effort-type signal processing application 300 to alternately use the first virtual memory area 200a, the second virtual memory area 200b, and the third virtual memory area 200c for the write and read of the real-time signal processing application 100 and the best effort-type signal processing application 300. Thereby, the real-time signal processing application 100 and the best effort-type signal processing application 300 can share data without interfering with each other's operations, and the real-time performance of the real-time signal processing application 100 is maintained.

Furthermore, the real-time signal processing application 100, the best effort-type signal processing application 300, and the control application 500 are arranged in the container virtual environment on the signal processing server as independent containers. Thereby, by containerizing the applications, the computer resources of the real-time signal processing application 100 and the best effort-type signal processing application 300 can be logically separated. Furthermore, by allocating the resources such as the CPU and GPU of the signal processing server 20 according to the priority, the computer resources of the applications can be logically separated.

Modification of First Embodiment

The medical information control system 1 according to the first embodiment has one real-time signal processing application 100 included in the signal processing server 20, but the medical information control system 1 according to a modification of the first embodiment is different in that the signal processing server 20 includes a plurality of real-time signal processing applications 100. Hereinafter, the difference from the medical information control system 1 according to the first embodiment will be described.

FIG. 11 is a block diagram illustrating a configuration example of the signal processing server 20 according to the modification of the first embodiment. As illustrated in FIG. 11, the signal processing server 20 includes a plurality of real-time signal processing applications 100. With such a configuration, the signal processing server can provide the real-time signal processing applications 100 to the plurality of image reception devices 60.

Note that it is also possible to employ a configuration in which a plurality of the best effort-type signal processing applications 300 is combined, or a configuration in which three or more applications are combined. For example, the signal processing server 20 can include a plurality of the real-time signal processing applications 100 and a plurality of the best effort-type signal processing applications 300. In this way, the signal processing server 20 can be configured according to various requirements.

Second Embodiment

A medical information control system 1 according to a second embodiment is different from the medical information control system 1 according to the first embodiment in that superimposition processing in consideration of a delay time by a best effort-type signal processing application 300 is also possible. Hereinafter, the difference from the medical information control system 1 according to the first embodiment will be described.

FIG. 12 is a block diagram illustrating a configuration example of a signal processing server 20 according to the second embodiment. As illustrated in FIG. 12, an input image 602 distributed to a virtual shared buffer 200 has a metadata area 6020 to which a timestamp or a serial number ID is added, and a difference value area 6022. Similarly, an output image 604 has a metadata area 6040a to which a timestamp or a serial number ID is added.

As described above, the best effort-type signal processing application 300 often has a lower frame rate or varies in processing time as compared with a real-time signal processing application 100. At that time, an output (superimposed image) of the best effort-type signal processing application 300 to be superimposed on an output of the real-time signal processing application 100 is temporally delayed. Operability of a user will be affected depending on the degree of the delay.

In contrast, in the best effort-type signal processing application 300 according to the present embodiment, processing of correcting the time is performed in consideration of the above delay. For example, in the present embodiment, processing of predicting and outputting a future value for the delayed time is performed. Furthermore, if the delay is equal to or higher than a certain level, processing of displaying the delay as an alert can be performed.

Hereinafter, a more specific description will be given. In FIG. 12, time-series passage of time in timestamp transfer processing is illustrated in order of A→B→C→D→E→F→G.

In A, when receiving an input of the input image 602 from an image imaging device 10, the real-time signal processing application 100 gives a timestamp (current time) as metadata to the metadata area 6020 of the input image 602. Then, the real-time signal processing application 100 writes the input image 602 to a virtual shared buffer 200. Furthermore, the real-time signal processing application 100 sends the input image 602 to its own pipeline. For example, the real-time signal processing application 100 performs processing of transferring image data with the timestamp in the signal processing A→the signal processing B→and the like.

Next, in B, the best effort-type signal processing application 300 reads the input image 602 with the timestamp via the virtual shared buffer 200 and sends the image data with the timestamp to its own pipeline (transfers the image data with the timestamp in the signal processing C→the signal processing D→and the like).

Next, in C, when performing an output to a virtual shared buffer 400, the best effort-type signal processing application 300 gives a value of the timestamp added to the input image 602 flowing through the pipeline to the metadata area 6040a of the corresponding output image (superposed image) data 604 as metadata, and writes the metadata in the virtual shared buffer 400.

Next, in D, the real-time signal processing application 100 reads the superimposed image data 604 with the timestamp from the virtual shared buffer 400. The real-time signal processing application 100 compares the superimposed image data 604 with the timestamp with the timestamp given to the input image 602 flowing through its own pipeline. As described above, since the read and write of the virtual shared buffers 200 and 400 are asynchronously performed, the former is considered to be an older value than the latter. The real-time signal processing application 100 calculates this difference value.

Next, in E, the real-time signal processing application 100 also gives the difference value calculated in D to the difference value area 6022 of the input image 602 as metadata in addition to the timestamp in A, and outputs the metadata to the virtual shared buffer 200.

Next, in F, the best effort-type signal processing application 300 reads the difference value given to the input image 602 read through the virtual shared buffer 200 and sends the difference value to its own pipeline in a similar manner to B.

Next, in G, the best effort-type signal processing application 300 regards the difference value given to the input image 602 as a delay, and performs the time correction for the delay in the signal processing (predicts a future value by the difference and performs the signal processing). Alternatively, the best effort-type signal processing application 300 draws an alert indicating the delay on the superposed image when performing an output to the virtual shared buffer 400.

Next, the real-time signal processing application 100 superposes the result image in G and outputs the image to the image reception device 60 via the IP converter 50. Note that the present embodiment is assumed to use the timestamp but the idea does not change even with a serial number ID.

As described above, the medical information control system 1 according to the present embodiment measures the delay time of the best effort-type signal processing application 300 with respect to the real-time signal processing application 100, and performs the time correction corresponding to the delay time. As a result, the positional shift of the best effort-type signal processing application 300 with respect to the real-time signal processing application 100 due to the delay time can be suppressed in an output image 606.

Third Embodiment

A medical information control system 1 according to a third embodiment is different from the medical information control system 1 according to the second embodiment in that superimposition processing in consideration of a processing change in a real-time signal processing application 100 is also possible. Hereinafter, the difference from the medical information control system 1 according to the second embodiment will be described.

FIG. 13 is a block diagram illustrating a configuration example of a signal processing server 20 according to the third embodiment. As illustrated in FIG. 13, an input image 602 is distributed to a virtual shared buffer 200, and further has a metadata area 6024 to which metadata other than a timestamp can be given. An image transmission device 10 according to the present embodiment corresponds to an image imaging device.

Here, a case in which signal processing 100g of a real-time signal processing application 100 performs zooming of an image, and a best effort-type signal processing application operates forceps recognition application will be described.

First, the signal processing 100g of the real-time signal processing application 100 performs zoom processing for the image 602 and generates a zoom image 6028.

Next, the real-time signal processing application 100 applies a zoom magnification of the signal processing 100g of the real-time signal processing application 100 to the metadata area 6024 of the input image 602. The signal processing 200g for drawing bounding boxes of the best effort-type signal processing application 300 reflects the amount of magnification given to the metadata area 6024 when drawing the bounding boxes. Moreover, a bounding box 6042 is drawn with a corresponding zoom factor of 1.5× so when it is ultimately superimposed on the zoomed image 6028, the contents of the buffer 6042, which was produced by the signal processing 300a (input), 300b (forceps recognition), 300g (bounding box generation), and output 300d, aligns with the content shown in the zoomed image 6028.

In this way, the magnification is typically transferred from the real-time signal processing application 100 to the best effort-type signal processing application 300 as metadata of the virtual shared buffer 200. Thereby, the best effort-type signal processing application 300 can reflect the magnification when drawing the bounding boxes of forceps. Therefore, the drawing of the forceps recognition result can be matched with the zoom processing of the real-time signal processing application 100, and it is possible to follow a smooth animation even in the case of zooming while changing the magnification. An output image 6060 is provided to an image reception device 60, which the content of the image 6042 with transparency is superimposed on the zoomed image 6028. The content of the image 6042 with transparency is produced on a best-effort basis, and thus may not be updated in real time. Nevertheless, the content of the image 6042 with transparency does not completely obscure the underlying zoomed image 6028 in the output image 6060 so a surgeon or other medical practitioner does not become frustrated by having part of the surgical site fully obscured with the content superimposed on the zoomed image 6028.

Fourth Embodiment

FIG. 14 is a block diagram that is similar to the configuration shown in FIG. 13, except the server includes two graphics processing units (GPUs), GPU #1 1441, and GPU #2 1442. Furthermore, GPU #2 1442 runs multiple best-effort applications, each having its own output shared buffer 1405, and 1407, as well as a shared input shared buffer 1403, which will be discussed in greater detail with respect to FIG. 16. In the configuration of FIG. 14, GPU #1 1441 runs a real-time application, which means it processes each frame from the medical imaging device as it is received, and outputs frames at a substantially same rate that the frames are input within a certain time frame (a small processing delay that is not generally perceivable by the surgeon). An example input frame 1410 is show after being processed by multiple signal processing processes, shown as Signal Processing A, and Signal Processing B, but it should be understood that more that two processes may be performed in real time on the GPU #1. The zoom application of the third embodiment is merely an example on one type of signal processing process that may be applied to the image frame provided by the medical imaging device.

Output from a shared buffer 1405 provides overlay content 1430 that is produced by a best-effort application #2, which includes Signal Processing C and Signal processing D, performed in GPU #2 1460. In this example, the overlay content 1430 are medical device/tool detection boundary boxes 1431, 1432 and 1433. Although not necessarily produced in real-time the medical device/tool detection boundary boxes 1431, 1432 and 1433 identify the medical instruments present in the surgical image as shown in the output image 1450. Similarly, a best-effort application #1 is performed in GPU #2 by applying Signal Processing C, and Signal Processing D to the input image stream provided from the medical image device via shared buffer 1403. In this exemplary case, the best-effort application #1 detects areas in which tissue in the surgical scene shows active bleeding. In this example, two bounding boxes 1421 and 1422 are part of the overlay content 1420 provided by the best-effort application #1, and are ultimately overlaid on the image 1410 with a degree of transparency so as identify bleeding sites in the output image 1450. The output image includes overlayed bounding boxes produced by the best-effort applications executed on GPU #2 1442 (each having a degree of transparency, although opaque is also an option) to identify image features in the real-time imagery provided by the real-time application provided by GPU #1 1441. The composite image is output as output image 1450.

In FIG. 14 a shared buffer 1403 is shown as hosted on GPU #2, rather than hosted on GPU #1. While it is possible to host the shared buffer 1403 on the GPU #1, the inventor recognized that such a configuration would require transferring twice as much data between GPUs, which would create a load on the GPU #1 that is already responsible for performing real-time processing. In contrast, by hosting the shared buffer on GPU #2, only half of the data needs to be conveyed over intra-GPU bus 1501 (FIG. 15). While GPU #2 is shown to host two best-effort applications, GPU #2 could also host more applications on a best-effort basis. Even if N applications are performed on GPU #2, as long as the shared buffer 1403 is hosted on GPU #2, there is no further expansion of data bus usage, nor inter-processor communication load on GPU #1, and thus the configuration promotes scalability for supporting more best-effort applications on the GPU #2.

FIG. 16 shows the internal operations and structure of the shared buffer 1403. While the structure of shared buffer 1403 is shown as having four internal dual-port shared buffers (Buffer 1, Buffer 2, Buffer 3, and Buffer 4), this structure is merely an example. More generally the shared buffer 1403 is an N+2 buffer, where N is the number of "consumer processes" (or best-effort applications) that are fed by the shared buffer 1403. In this context more than N+2 internal buffers may be used, although with more than 2 additional buffers at least one of the internal buffers will not be used by either the input (producer process, such as image data from the medical imaging device provided through the distribution processing hosted on GPU #1) or the consumer processes. The reason for two (or even more) additional buffers is described below with respect to FIG. 16.

It should first be understood that while the input side is busy storing data in particular buffers (e.g., store data D1 in Buffer B1), the data in Buffer 1 is not stable and thus not ripe to be retrieved. However, once D1 is fully written to Buffer 1, consumer processes 1 and 2 (CP1 and CP2) are able to retrieve it. Once the producer process is finished writing D1 to Buffer 1, the shared buffer 1403 can indicate that Buffer 1 is stable by any number of ways such as controller monitor, flag setting, etc.

Once D1 is stored in Buffer 1, the producer process starts to write data D2 in Buffer 2 (or another one of the N+1) buffers. Buffer 1 is then available to be accessed by CP1 and CP2. Once D2 is written to Buffer 2, it may then be accessed by CP1 and CP2. However, CP1 may have a faster throughput than CP2, and thus CP2 accesses Buffer 2 after CP1 begins to access Buffer 2. Thus, CP1 and CP2 may not be synchronized in their access and so it follows that for every N best-effort applications, they will be accessing N buffers at any given time. However, the producer process cannot simultaneously be storing data in any of those N buffers at the same time. Accordingly, an additional buffer will be active for storing data therein, making a total of N+1 buffers. However, once the producer process is about to finish storing data in one internal buffer, it needs to know the next available buffer so it can immediately fill that buffer with incoming data so an overload situation does not arise. Moreover, the producer process needs to know the next available buffer in addition the present buffer it is filling. Accordingly, the input side (i.e., the producer process) needs two buffers to operated independently (and not require coordination with CP1 or CP2), and so a total of N+2 buffers are needed to support independent and asynchronous input and output operations-N buffers for N best effort applications, and 2 additional internal buffers to support the producer process writing data to the shared buffer 1403. It should further be mentioned that CP1 and CP2 are applications that may not need all of the input data. For example, CP2 may be a processor intensive process, and not necessary to analyze all of the image data. In this case, CP2 may access the data in the internal buffers at a much slower rate than CP1, and as such CP2 may only read every second/third/fourth . . . data entry in the buffer 1403.

Optionally, CP1 and/or CP2 may operate in a wait mode, especially if CP1 and CP2 start reading at the same speed or at the same timing. In other words, suppose it is desirable for CP1 to process the same data as CP2, but CP2 reads data slower than CP1. In this case CP1 can be placed in a wait mode to wait for CP2 to finish its reading of the previous buffer before CP1 reads the next buffer along with CP2. CP1 can also be placed in wait mode if writing to the next buffer is not complete. An advantage to CP1 operating in wait mode is that CP1 may have a lower latency requirement than CP2, and therefore there is an advantage to set the consumer process with shortest latency (delay from input to output) to the wait mode.

The shared buffer may have more than N+2 buffers, where additional buffers beyond the N+2 are kept in reserve in case an additional process, CP3, comes on-line. When CP3 comes on-line the producer process will not write to a fifth internal buffer, where N is now 3 (5=N (now 3)+2). Similarly, if a CP goes off-line, then an internal buffer may be taken off-line and kept in reserve.

Note that the present technology can also have the following configurations.

(1) A medical information control system including:
    an operation server connected to a medical device in an operation room via a network and in which a container virtual environment is build, the operation server including
a plurality of virtual shared buffers to which a first medical application and a second medical application are accessible, the first medical application being installed in a first container virtual area and being configured to perform first processing on the basis of information output from the medical device to generate first medical information, and the second medical application being installed in a second container virtual area and being configured to perform second processing having a processing amount different from the first processing to generate second medical information, and
a control application,
the plurality of virtual shared buffers each having a first virtual memory area, a second virtual memory area, and a third virtual memory area, and
the control application being configured to control the first medical application or the second medical application to alternately use the first virtual memory area, the second virtual memory area, and the third virtual memory area for write of the first medical application and read of the second medical application.

(2) The medical information control system according to (1), in which the second medical application is larger than the first medical application in the processing amount.

(3) The medical information control system according to (1), in which the second medical application is signal processing in which the processing amount varies according to content of an input image to be processed.

(4) The medical information control system according to (3), in which
the first medical application supplies the input image to the second medical application via an input-side virtual shared buffer of the plurality of virtual shared buffers, and
the second medical application generates the second medical information on the basis of the input image, and supplies the second medical information to the first medical application via an output-side virtual shared buffer of the plurality of virtual shared buffers.

(5) The medical information control system according to (4), in which the second medical application generates first medical information in time series on the basis of the input image supplied in time series, and adds information based on the second medical information supplied via the output-side virtual shared buffer to the first medical information and outputs the first medical information with the added information.

(6) The medical information control system according to (4) or (5), in which the second medical application generates the second medical information by predictive processing according to a processing time.

(7) The medical information control system according to (6), in which
a delay time of the second medical application is measured on the basis of a start time of processing and an end time of the processing associated with the input image, and
the second medical application performs the predictive processing on the basis of the delay time.

(8) The medical information control system according to any one of (4) to (7), in which the second medical application generates information indicating position information generated by the signal processing for the input image on an image with transparency, and the second medical application superimposes the image with transparency supplied via the output-side virtual shared buffer and an image based on the input image, using the transparency.

(9) The medical information control system according to (8), in which the signal processing for the input image is recognition processing for at least one of forceps or a bleeding portion.

(10) The medical information control system according to any one of (4) to (9), in which the first medical application supplies information regarding a change in signal processing in the first medical application in association with the input image to the second medical application, and the second medical application changes the signal processing on the basis of the information regarding a change in signal processing.

(11) The medical information control system according to any one of (1) to (10), further including:
a medical imaging device;
an input-side IP converter configured to change a medical image captured by the medical imaging device into a predetermined image format;
an IP switch configured to switch a supply destination of the medical image in the predetermined image format and a processed image supplied from the operation server, and capable of supplying the medical image in the predetermined image format to the operation server;
an output-side IP converter configured to change the image supplied from the IP switch into a predetermined image format; and
an image reception device configured to display an image supplied from the output-side IP converter.

(12) The medical information control system according to (11), in which at least one of the IP converter, the IP switch, or the operation server executes processing on the basis of a control command acquired from another device.

(13) A signal processing device for operation connected to a medical device in an operation room via a network and in which a container virtual environment is build,
the signal processing device including:
a plurality of virtual shared buffers to which a first medical application and a second medical application are accessible, the first medical application being installed in a first container virtual area and being configured to perform first processing on the basis of information output from the medical device to generate first medical information, and the second medical application being installed in a second container virtual area and being configured to perform second processing having a processing amount different from the first processing to generate second medical information; and
a control application,
the plurality of virtual shared buffers each having a first virtual memory area, a second virtual memory area, and a third virtual memory area, and
the control application being configured to control the first medical application or the second medical application to alternately use the first virtual memory area, the second virtual memory area, and the third virtual memory area for write of the first medical application and read of the second medical application.

(14) A medical information control method of a signal processing device connected to a medical device in an operation room via a network and in which a container virtual environment is build,
the signal processing device including
a plurality of virtual shared buffers to which a first medical application and a second medical application are accessible, the first medical application being installed in a first container virtual area and being configured to perform first processing on the basis of information output from the medical device to generate first medical information, and the second medical application being installed in a second container virtual area and being configured to perform second processing having a processing amount different from the first processing to generate second medical information, and a control application, the plurality of virtual shared buffers each having a first virtual memory area, a second virtual memory area, and a third virtual memory area, in which the control application controls the first medical application or the second medical application to alternately use the first virtual memory area, the second virtual memory area, and the third virtual memory area for write of the first medical application and read of the second medical application.

Note that the present technology can also have the following configurations.

(1) A medical information control system comprising:
an operation server connected to a medical imaging device in an operation room via a network, wherein the operation server includes processing circuitry configured to:
obtain a medical imaging stream of a medical video generated by the medical imaging device,
execute, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable, and
superimpose the processing result of the best effort medical processing application on images contained in the medical imaging stream processed by the real-time medical processing application.

(2) The medical information control system according to (1), wherein the best-effort basis being real-time under a condition where available processing resources are sufficient to provide real-time processing, and less than real-time under a condition where available processing resources are not sufficient to provide real-time processing.

(3) The medical information control system according to (2), wherein the condition where available processing resources are not sufficient to provide real-time medical processing exists when unallocated processing resources are insufficient to perform processing on sequential frames of the medical imaging stream.

(4) The medical information control system according to (1), wherein the real-time medical processing application and the best effort processing application are containerized applications in the container virtual area that uses a virtualized operating system.

(5) The medical information control system according to (1), further comprising an application that is executed on a virtual machine, wherein the virtual machine being hosted on different hardware than the container virtual area.

(6) The medical information control system according to (1), wherein the best effort medical processing application requires greater processing capacity when processing the medical imaging stream in real-time than the real-time medical processing application.

(7) The medical information control system according to (1), wherein an amount of processing capacity required to support the best effort medical processing application varies according to a content of image frames provided by the medical imaging device.

(8) The medical information control system according to (1), wherein the best effort medical processing application applies predictive processing according to a processing time on at least one frame of the medical imaging stream to generate the processing result.

(9) The medical information control system according to (8), wherein
a delay time of the best effort medical processing application is measured on a basis of a start time of processing and an end time of the processing associated with the at least one frame, and
the best effort medical processing application performs the predictive processing on a basis of the delay time.

(10) The medical information control system according to (1), wherein the best effort medical processing application generates information indicating position information as the processing result that is superimposed in a transparent fashion on the medical imaging stream processed by the real-time medical processing application.

(11) The medical information control system according to (10), wherein the processing result includes a recognition by the best effort medical processing application of at least one of forceps or a bleeding portion contained in the medical video.

(12) A medical information control method comprising:
obtaining by an operation server connected to a medical imaging device in an operation room via a network a medical imaging stream of a medical video generated by the medical imaging device;
executing, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable; and
superimposing the processing result of the best effort medical processing application on images contained in the medical imaging stream processed by the real-time medical processing application.

(13) The medical information control method according to (12), wherein the best-effort basis being real-time under a condition where available processing resources are sufficient to provide real-time processing, and less than real-time under a condition where available processing resources are not sufficient to provide real-time processing.

(14) The medical information control method according to (13), wherein the condition where available processing resources are not sufficient to provide real-time medical processing exists when unallocated processing resources are insufficient to perform processing of sequential frames on the medical imaging stream.

(15) The medical information control method according to (12), wherein the real-time medical processing application and the best effort processing application are containerized applications in the container virtual area that uses a virtualized operating system.

(16) The medical information control method according to (12), further comprising executing an application that is executed on a virtual machine, wherein the virtual machine being hosted on different hardware than the container virtual area.

(17) The medical information control method according to (12), wherein the best effort medical processing application requires greater processing capacity when processing the medical imaging stream in real-time than the real-time medical processing application.

(18) The medical information control method according to (12), wherein an amount of processing capacity required to support the best effort medical processing application varies according to a content of image frames provided by the medical imaging device.

(19) The medical information control method according to (12), wherein the executing the best effort medical processing application includes applying predictive processing according to a processing time on at least one frame of the medical imaging stream to generate the processing result.

(20) A non-transitory computer readable storage device having computer readable instructions stored therein that when executed by an operation server performs a medical information control method, the method comprising:
    obtaining by the operation server connected to a medical imaging device in an operation room via a network a medical imaging stream of a medical video generated by the medical imaging device;
    executing, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable; and
    superimposing the processing result of the best effort medical processing application on images contained in the medical imaging stream processed by the real-time medical processing application.

The aspects of the present disclosure are not limited to the above-described individual embodiments, but also include various modifications that can be conceived by those skilled in the art, and the effects of the present disclosure are not limited to the above-described content. That is, various additions, changes, and partial deletions are possible without departing from the conceptual idea and purpose of the present disclosure derived from the content defined in the claims and its equivalents.

REFERENCE SIGNS LIST

1 Medical information control system
10 Medical imaging device
20 Signal processing server
30 IP converter
40 IP switch
50 IP converter
50 Real-time signal processing application
200 Virtual shared buffer
300 Best effort-type signal processing application
400 Virtual shared buffer
500 Control application

The invention claimed is:
1. A medical information control system comprising:
    an operation server connected to a medical imaging device in an operation room via a network, wherein the operation server includes processing circuitry configured to:
    obtain a medical imaging stream of a medical video generated by the medical imaging device,
    execute, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable, and
    superimpose the processing result of the best effort medical processing application on images contained in the medical imaging stream processed by the real-time medical processing application.

2. The medical information control system according to claim 1, wherein the best-effort basis being real-time under a condition where available processing resources are sufficient to provide real-time processing, and less than real-time under a condition where available processing resources are not sufficient to provide real-time processing.

3. The medical information control system according to claim 2, wherein the condition where available processing resources are not sufficient to provide real-time medical processing exists when unallocated processing resources are insufficient to perform processing on sequential frames of the medical imaging stream.

4. The medical information control system according to claim 1, wherein the real-time medical processing application and the best effort processing application are containerized applications in the container virtual area that uses a virtualized operating system.

5. The medical information control system according to claim 1, further comprising an application that is executed on a virtual machine, wherein the virtual machine being hosted on different hardware than the container virtual area.

6. The medical information control system according to claim 1, wherein the best effort medical processing application requires greater processing capacity when processing the medical imaging stream in real-time than the real-time medical processing application.

7. The medical information control system according to claim 1, wherein an amount of processing capacity required to support the best effort medical processing application varies according to a content of image frames provided by the medical imaging device.

8. The medical information control system according to claim 1, wherein the best effort medical processing application applies predictive processing according to a processing time on at least one frame of the medical imaging stream to generate the processing result.

9. The medical information control system according to claim 8, wherein
    a delay time of the best effort medical processing application is measured on a basis of a start time of processing and an end time of the processing associated with the at least one frame, and
    the best effort medical processing application performs the predictive processing on a basis of the delay time.

10. The medical information control system according to claim 1, wherein the best effort medical processing application generates information indicating position information as the processing result that is superimposed in a transparent fashion on the medical imaging stream processed by the real-time medical processing application.

11. The medical information control system according to claim 10, wherein the processing result includes a recognition by the best effort medical processing application of at least one of forceps or a bleeding portion contained in the medical video.

12. A medical information control method comprising:
obtaining by an operation server connected to a medical imaging device in an operation room via a network a medical imaging stream of a medical video generated by the medical imaging device;
executing, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable; and
superimposing the processing result of the best effort medical processing application on images contained in the medical imaging stream processed by the real-time medical processing application.

13. The medical information control method according to claim 12, wherein the best-effort basis being real-time under a condition where available processing resources are sufficient to provide real-time processing, and less than real-time under a condition where available processing resources are not sufficient to provide real-time processing.

14. The medical information control method according to claim 13, wherein the condition where available processing resources are not sufficient to provide real-time medical processing exists when unallocated processing resources are insufficient to perform processing of sequential frames on the medical imaging stream.

15. The medical information control method according to claim 12, wherein the real-time medical processing application and the best effort processing application are containerized applications in the container virtual area that uses a virtualized operating system.

16. The medical information control method according to claim 12, further comprising executing an application that is executed on a virtual machine, wherein the virtual machine being hosted on different hardware than the container virtual area.

17. The medical information control method according to claim 12, wherein the best effort medical processing application requires greater processing capacity when processing the medical imaging stream in real-time than the real-time medical processing application.

18. The medical information control method according to claim 12, wherein an amount of processing capacity required to support the best effort medical processing application varies according to a content of image frames provided by the medical imaging device.

19. The medical information control method according to claim 12, wherein the executing the best effort medical processing application includes applying predictive processing according to a processing time on at least one frame of the medical imaging stream to generate the processing result.

20. A non-transitory computer readable storage device having computer readable instructions stored therein that when executed by an operation server performs a medical information control method, the method comprising:
obtaining by the operation server connected to a medical imaging device in an operation room via a network a medical imaging stream of a medical video generated by the medical imaging device;
executing, a real-time medical processing application and a best effort medical processing application installed in a container virtual area, wherein the real-time medical processing application performs image processing on the medical imaging stream in real-time, and the best effort medical processing application performs analysis processing based on the medical imaging stream on a best-effort basis, identification of the real-time medical processing application and the best effort medical processing application being user selectable; and
superimposing the processing result of the best effort medical processing application on images contained in the medical imaging stream processed by the real-time medical processing application.

* * * * *